(12) United States Patent
Keener et al.

(10) Patent No.: US 11,166,481 B2
(45) Date of Patent: Nov. 9, 2021

(54) SYSTEMS AND METHODS FOR REACTIVE GAS-BASED PRODUCT TREATMENT

(71) Applicant: Clean Crop Technologies, Inc., Haydenville, MA (US)

(72) Inventors: Kevin M. Keener, Ames, IA (US); Daniel White, Chesterfield, MA (US); Daniel Cavanaugh, Alexandria, VA (US); Yaqoot Shaharyar, Northampton, MA (US)

(73) Assignee: CLEAN CROP TECHNOLOGIES, INC., Haydenville, MA (US)

( * ) Notice: Subject to any disclaimer, the term of this patent is extended or adjusted under 35 U.S.C. 154(b) by 0 days.

(21) Appl. No.: 17/081,837

(22) Filed: Oct. 27, 2020

(65) Prior Publication Data

US 2021/0120848 A1   Apr. 29, 2021

Related U.S. Application Data

(60) Provisional application No. 62/926,933, filed on Oct. 28, 2019.

(51) Int. Cl.
| | | |
|---|---|---|
| *A23L 3/26* | (2006.01) | |
| *A23B 9/06* | (2006.01) | |
| *A23L 3/32* | (2006.01) | |
| *A61L 2/14* | (2006.01) | |
| *B01J 7/00* | (2006.01) | |

(52) U.S. Cl.
CPC ........ *A23L 3/26* (2013.01); *A23B 9/06* (2013.01); *A23L 3/32* (2013.01); *A61L 2/14* (2013.01); *B01J 7/00* (2013.01); *A23V 2002/00* (2013.01)

(58) Field of Classification Search
CPC .... A23B 9/06; A23B 9/16; A23B 9/18; A23B 9/20; A23B 9/22; A23L 3/26; A23L 3/263; A23L 3/266; A23L 3/28; A23L 3/32; A23L 3/325; A23L 3/34; A23L 3/3409; A23L 3/34095; A23L 3/3418; A23L 3/3445; A61L 2/14
See application file for complete search history.

(56) References Cited

U.S. PATENT DOCUMENTS

| | | | |
|---|---|---|---|
| 6,441,554 B1 * | 8/2002 | Nam .................. | A61L 9/22 |
| | | | 118/723 R |
| 9,295,280 B2 * | 3/2016 | Jacofsky ............ | A23L 3/32 |
| 9,560,860 B2 * | 2/2017 | Zwijack ............ | A23B 9/22 |
| 10,194,672 B2 | 2/2019 | Keener et al. | |

* cited by examiner

*Primary Examiner* — Timothy C Cleveland
(74) *Attorney, Agent, or Firm* — Cantor Colburn LLP

(57) ABSTRACT

Systems and methods disclosed herein provide an improved high voltage plasma-based product treatment by integrating the plasma reactor into the processing container. This unique device can deliver a high throughput rate of raw food, without adverse effects on quality. The system is operationally efficient, and is capable of being scaled up or down to provide lower or higher throughput rates, depending on the product manufacturer or processor's needs. In particular, the system obviates the need for further containerization or packaging of product during pasteurization processing.

9 Claims, 27 Drawing Sheets
(7 of 27 Drawing Sheet(s) Filed in Color)

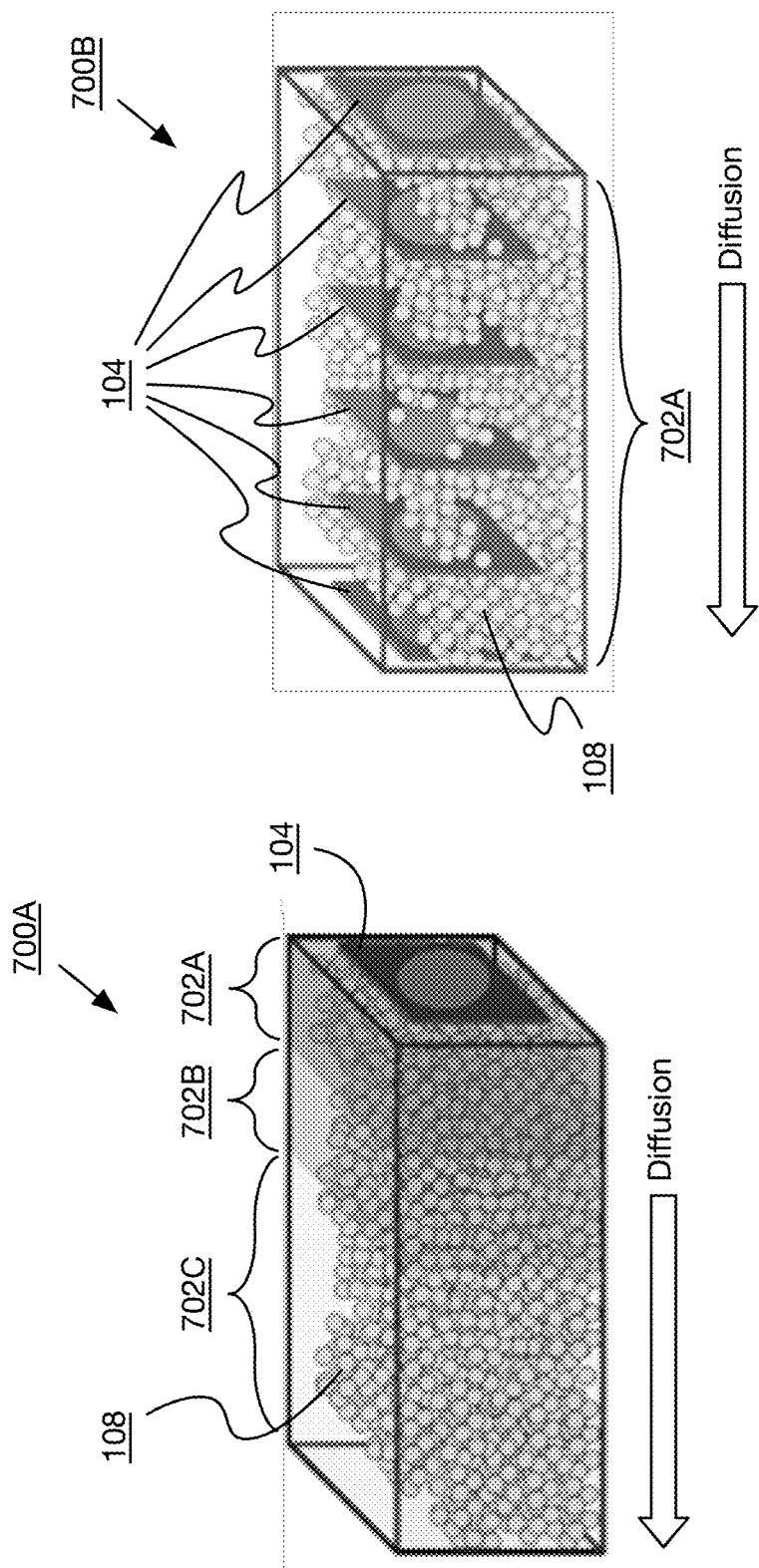

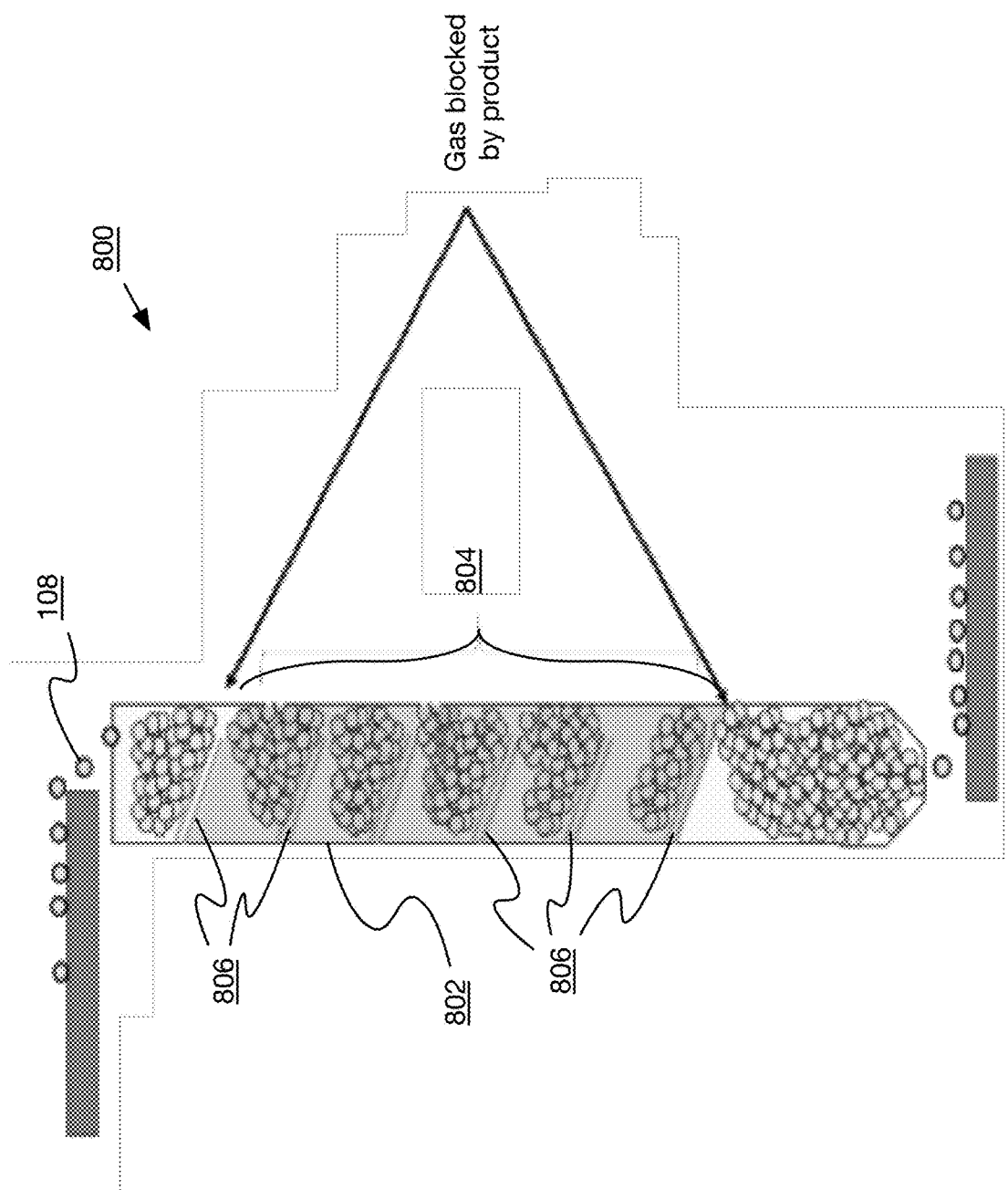

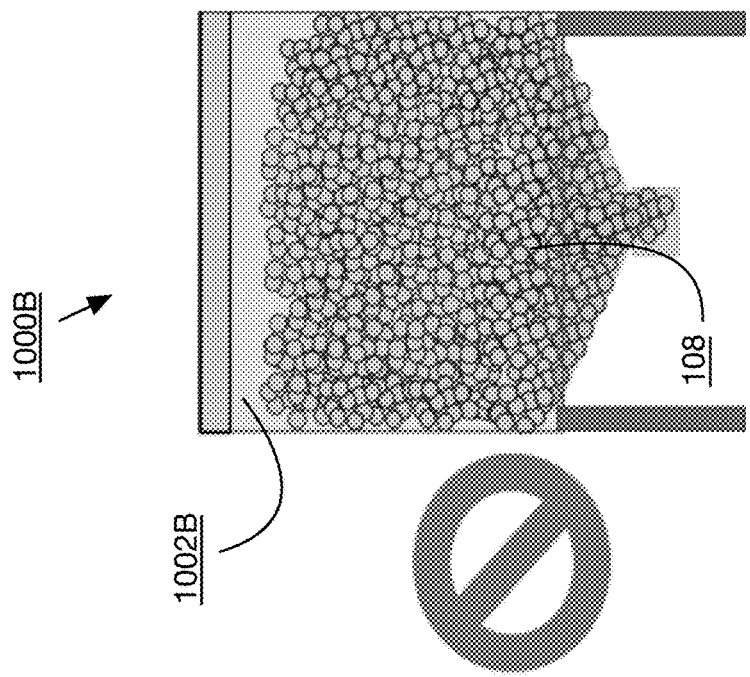
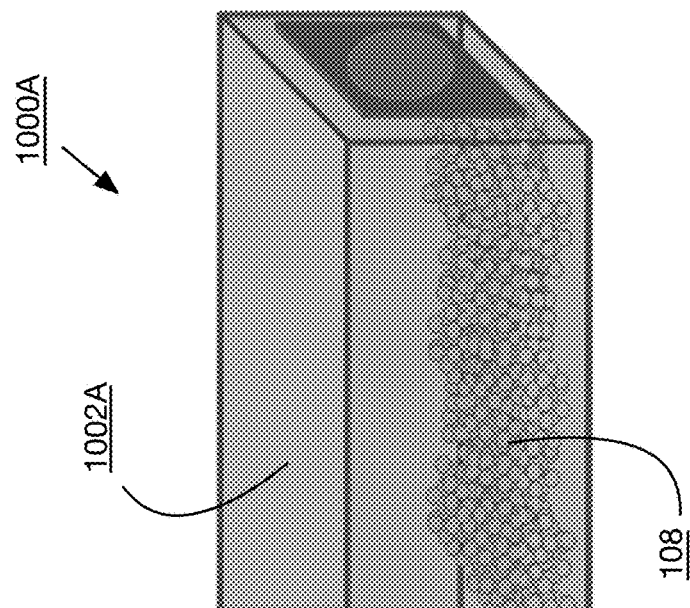
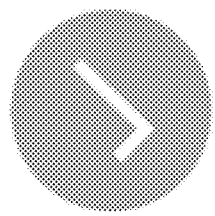
FIG. 10

SYSTEMS AND METHODS FOR REACTIVE GAS-BASED PRODUCT TREATMENT

RELATED APPLICATIONS

The present application claims the benefit of and priority to U.S. Provisional Patent Application No. 62/926,933, entitled "Systems and Methods for Reactive Gas-Based Product Treatment," filed Oct. 28, 2019, the entirety of which is incorporated by reference herein.

TECHNICAL FIELD

The present disclosure relates generally to systems and methods for cold plasma-based food or biological or medical or industrial product treatment.

BACKGROUND

Products and in particular food products such as nuts, grains, liquids and perishable goods may be susceptible to contamination from pathogens, microbes, viruses and various toxigenic compounds such as mycotoxins. Treating or sterilizing these products to enhance safety frequently involves the use of chemicals, intensive washing, physical segregation of contaminants and various thermal (high temperatures) treatments. that may adversely affect the quality of the product.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

FIGS. 7A and 7B are diagrams illustrating implementations of systems without interior reactive gas species generation and with interior reactive gas species generation, respectively;

FIG. 8 is a diagram of an implementation of a gravity-fed system for treating product;

FIG. 10 is an illustration of volume capacity during treatment, according to some implementations;

Figure 1:
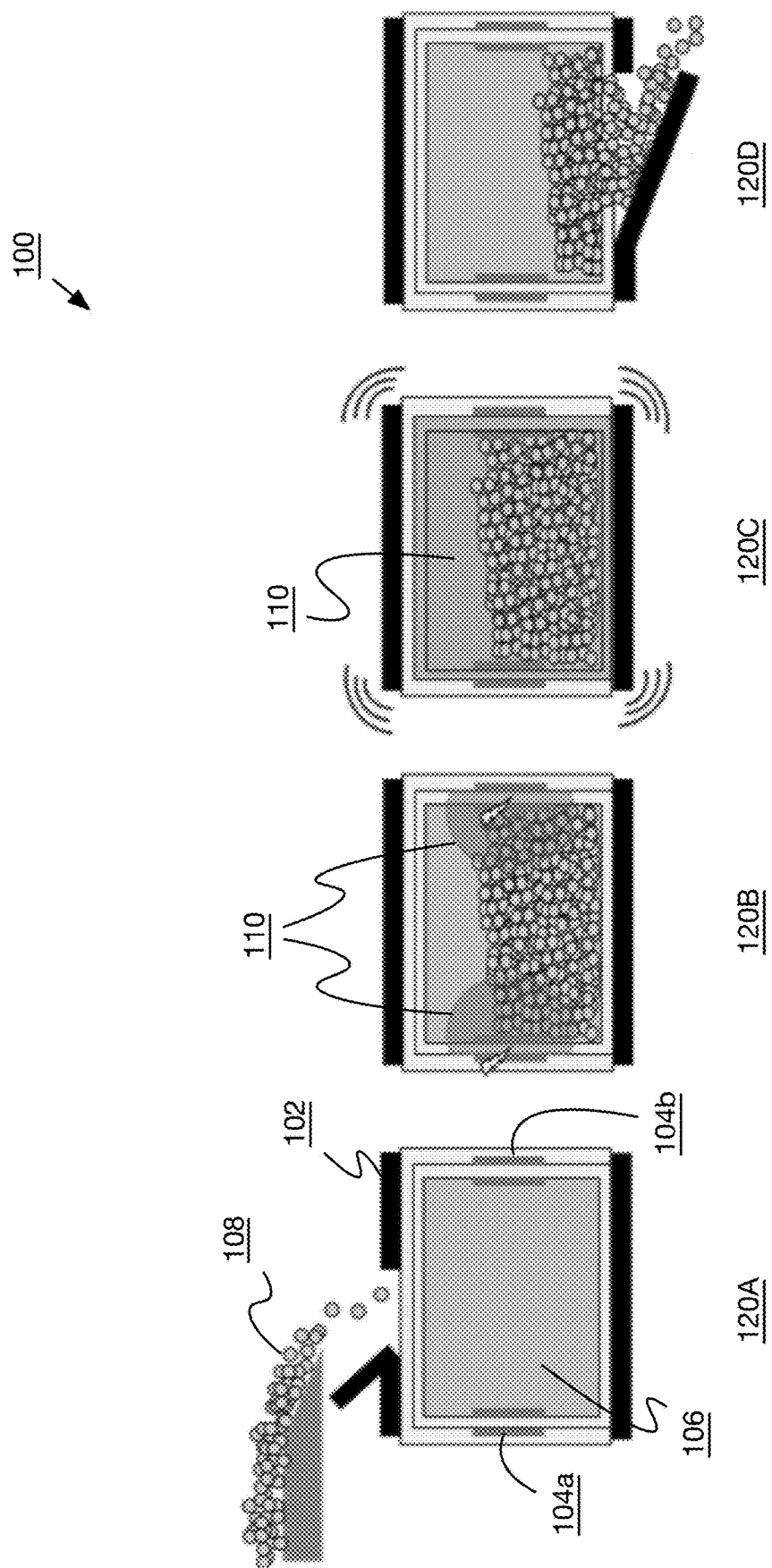
FIG. 1 is an illustration of a process for treating product, according to some implementations.

The details of various embodiments of the methods and systems are set forth in the accompanying drawings and the description below.

DETAILED DESCRIPTION

Products and in particular food products such as nuts and grains may be susceptible to contamination from mycotoxins and microbes. Treating or sterilizing these products to enhance safety frequently involves the use of high temperatures that may adversely affect the quality of the product. For example, thermal processing of a raw food to achieve pasteurization may cook the product, altering flavor and texture. For raw food products thermal treatments are undesirable in many grains, seeds and nuts.

Some efforts to mitigate this undesirable effect include pre-packaging the product, such as vacuum sealing the product in a container (e.g. a thin plastic bag) to prevent hot steam used for pasteurization from directly contacting the product. This still results in heating of the product that may be undesirable, and also adds expense to processing and limits throughput. For example, some processing systems may individually vacuum seal an amount of nuts as small as a kilogram or less before pasteurizing the product, while processing shipments as large as hundreds of kilograms.

High voltage plasmas may be used for product treatment in some implementations, allowing processing at lower temperatures, including room temperature (e.g. approximately 20 degrees Celsius). However, some implementations may require sealing the raw food product within a container, which may be limited in size and volume. Such implementations may suffer from the throughput deficiencies noted above due to the size limitations of the container enclosing the product and requirement to individually package the product or small groups of product.

The systems and methods discussed herein are directed to an improved high voltage plasma-based product treatment capable of processing product at a high throughput rate, without changing the visual or chemical composition of the product. The treatment does not create any significant change in the organoleptic properties of the product, or shorten the shelf-life such as with heating (thermal) treatments. The system design is modular which allows for variable throughput rates of treatment. This provides for flexible scaling of the technology in different processing environments which might require larger or smaller throughput (e.g. lbs/hour to tons/hour or more). The technology may be integrated into a containerized system where food products are introduced in a continuous flow or stagnant (bulk) arrangement. The treatment may also be operationally efficient, and is capable of being scaled up or down to provide lower or higher throughput rates, depending on the product manufacturer or processor's needs. In particular, by integrating the plasma reactor into the processing container, the system obviates the need for further containerization or packaging of product during processing. The system further allows for:

Adaptability: Implementations of the reactor are widely flexible in terms of material and geometry, and can be adapted into any container wall or component, including rigid sidewalls for pallet-based totes; circular or square sidewalls for grain bins; flexible bags or conveyor belts, etc.

Modularity: Because of the wide range of materials, flexibilities, and geometries to which the reactor can be conformed, implementations of the described system are completely modular: adding more reactor capacity can be scaled linearly with the treatment vessel/container size itself Cost/material efficiency: Integrating the reactor inside the container wall streamlines device material utilization, reducing cost, and reducing system complexity, in many implementations.

Worker safety: By integrating the reactor into the broader system materials, implementations of the system allow for greater distance between workers and high voltage electric generation, improving safety and reducing the risk of dangerous accidents. The device is also not restricted to plasma generation within a container. The production of reactive gas species and treatment of products may occur in an open system or any environment which includes products to be treated and ambient air. This is achieved through any of the different techniques discussed herein including controlled gas diffusion, in situ reactive gas species production within a gravity fed system, and variable geometries of plasma generation cells.

As discussed in more detail below, in tests, implementations of the described system reduced aflatoxin contamination in 200 grams of peanuts from 260 parts per billion (ppb) to 105 ppb, a 60% reduction, generating plasma at 50 kV for one hour; and to 67 ppb, a 74% reduction, running at 70 kV for one hour.

Although discussed primarily in terms of food products, the systems and methods discussed herein may be used for microbial or mycotoxin mitigation of any product, including sterilization of medical devices, food processing equipment, and industrial products without use of antibiotic or antifungal agents that may eventually lead to biologic immunity and reduced efficacy.

Referring first to FIG. 1, illustrated is a process 100 for treating product, according to some implementations. A container 102 may comprise a plurality of sidewalls, a top, and a bottom, enclosing a chamber 106. One or more of the sidewalls of the container may comprise plasma reactors 104a, 104b (referred to generally as plasma reactors 104 or reactors 104). A product 108 may be loaded into the container in a first step 120A. The container may be sealed, and a high voltage plasma 110 generated by reactors 104 at step 120B. The plasma 110 may be diffused through the chamber 106 and product 108 at step 120B. The plasma 110 may be generated by the reactors at voltages of 10 kV, 20 kV, 50 kV, 70 kV, 100 kV, 130 kV or any other such voltage, and may be allowed to diffuse through the chamber for any appropriate amount of time, such as 10 minutes, 20 minutes, 30 minutes, one hour, or any other such period at step 120C. The plasma may be substantially at room temperature, up to approximately 60 degrees Celsius. The plasma ionizes a gas, such as air, generating over 75 unique reactive gas species (RGS) if generated in ambient air, including $O_2$, $NO_2$, $NO_3$, $N_2O_4$, $N_2O_5$, $H_2O_2$, $N_2O$, OH or other such species, including but not limited to formic acid, peroxide ions, dinitrogen oxide, etc. The RGS have bactericidal, sporicidal, and fungicidal properties, and may significantly reduce the concentrations of mycotoxins or bacteria contaminating product 108. After being treated for the predetermined period of time, the chamber may be emptied of product at step 120D. The RGS products may convert back to their original gas states (e.g. $O_2$, $N_2$, $CO_2$, etc.), leaving no chemical residues. The product may accordingly be treated without adverse effects from heating or chemical contamination. The product may be discharged to ground, in many implementations, and the chamber may be evacuated of any remaining RGS (e.g. via a vacuum or fan).

The specific composition and proportions of each RGS may be determined by the treatment conditions and geometries of the plasma generation device. The specific composition of RGS generated may be changed or determined by a wide range of variables, including voltage, temperature, humidity, air pressure, air velocity, feed gas composition, product volume, treatment container volume, or other such variables.

Degradation, denaturation or inactivation of different toxins, pathogens and other food contaminants may require different varieties and quantities of RGS. The systems and methods discussed herein may employ treatment cycles with different rates, ranges and parameters of each of the above variables to produce specific 'cocktails' of RGSs for each food product and contamination issue.

In other devices which leverage the biocidal capabilities of 'cold plasma' without implementing the systems and methods discussed herein, this distinction has not been defined or differentiated. The generation of different gas species is critical to the performance of the system as otherwise the contaminants will otherwise not be removed or reduced. Accordingly, in some implementations, the systems discussed herein may be referred to as a multi-variable gas generation device. Depending on the type of contaminant, the device and treatment conditions (variables) can be adjusted to ensure the optimal amounts of RGSs are produced and applied to each product.

The flexible generation of gases is also important to the market value and scalability as a commercial food processing solution of the systems and methods discussed herein. In some instances, some RGSs may create a negative or undesirable effect on food quality. The systems and methods discussed herein use specific geometries and treatment parameters to ensure this does not occur.

In many implementations, ozone may be used as a feed gas in the treatment process. In some instances, after the high voltage current is turned off, many RGSs continue to be generated while ozone ($O_3$) gas rapidly declines. Accordingly, ozone may be a catalyst for many of the other RGSs generated in the process. This distinction is unique to implementations of the systems and methods discussed herein, as it allows for significantly more controlled generation of other RGSs. The integration of ozone as a feed gas may also substantially reduce the total energy consumption to generate a high volume of other RGSs with nitrate, nitrite, and peroxide characteristics.

Figure 2A:
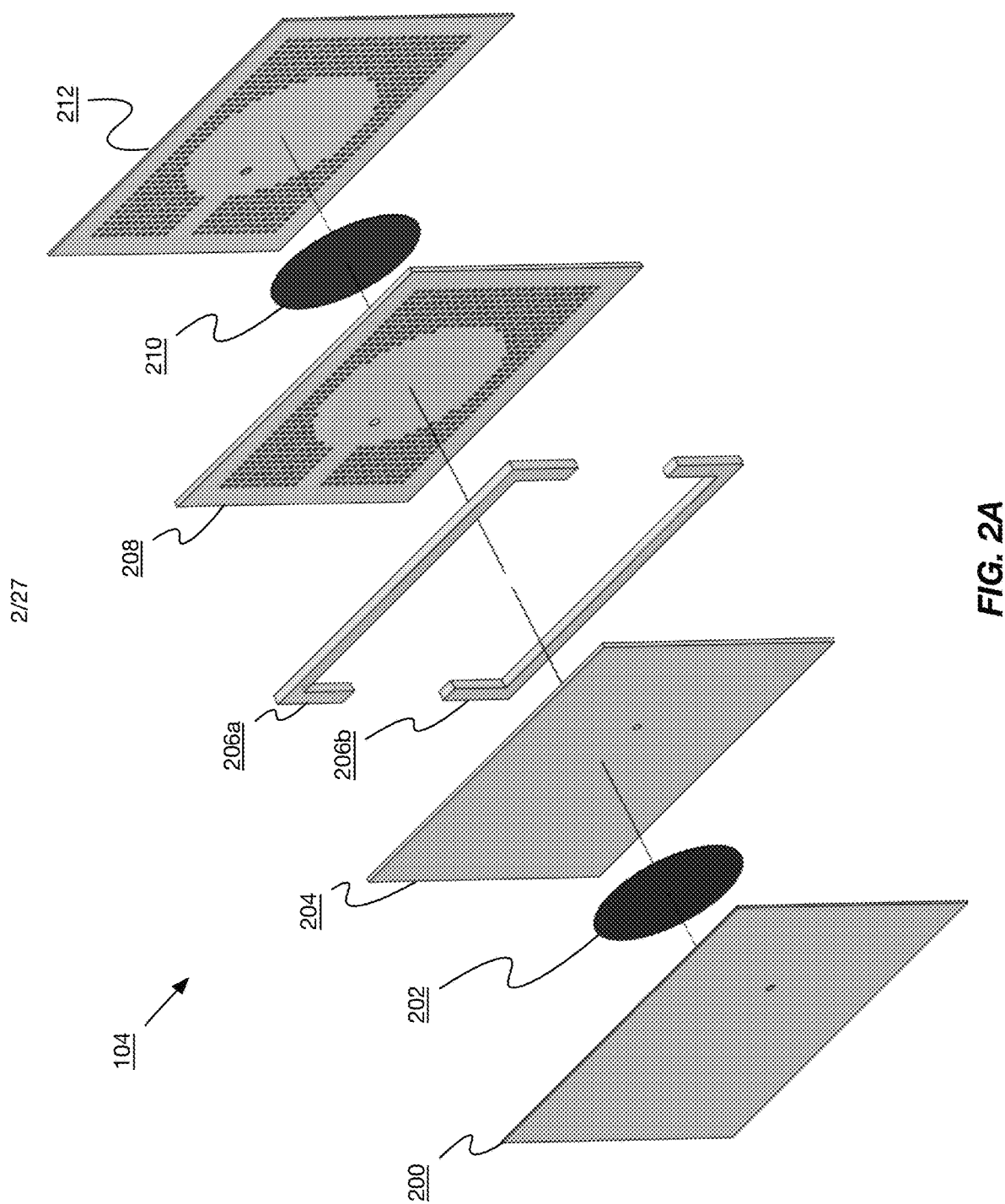
FIG. 2A is an exploded view of a cold plasma reactor, according to some implementations.

FIG. 2A is an exploded view of a cold plasma reactor 104, according to some implementations. The reactor 104 may include a plurality of layers 200-212, including:

Exterior Insulator 200: A sufficiently insulative non-conductive material layer, which may be at least ⅛" or more thickness in some implementations. The insulator 200 may be of any suitable material, such as polypropylene, Teflon, thermoplastic, or any other such non-conductive material.

Electrode 202: An electrode made of a conductive or non-conductive material capable of maintaining and distributing a high voltage electric field in excess of 10 kV, 20 kV, 30 kV, 50 kV, 70 kV, 100 kV, 120 kV, 250 kV, or any other such value, in a controlled manner, in various implementations. In many implementations, the electrode may comprise a conductive material, such as aluminum or copper, although other materials and shapes may be utilized.

Dielectric layer 204: A non-conductive material (glass, ceramic polymeric material, mica, natural or synthetic rubbers, etc.), which may be at least 1/16" or greater thickness in some implementations.

Frame 206a-206b (referred to generally as frame 206): A frame may support dielectric layer 204 and a dielectric layer 208, leaving an air gap, which may be of at least ¼" or greater in some implementations. Although shown in two parts, in some implementations, frame 206 may comprise a single piece. The frame may be open on one or more sides as shown, and may include interior supports in some implementations.

Dielectric layer 208: A non-conductive material (glass, ceramic, polymeric material, mica, natural or synthetic rubbers, etc.), which may be of at least 1/16" or greater thickness in some implementations. In many implementations, the dielectric layer 208 may be perforated as shown to allow air to pass between the air gap provided by frame 206 and a chamber of the container bounded by reactor 104. In many implementations, a portion of the dielectric layer 208 may be solid, e.g. to support an electrode 210 and associated wiring as shown.

Electrode 210: An electrode made of a conductive or non-conductive material capable of maintaining and distributing a high voltage electric field in excess of 10 kV, 20 kV, 30 kV, 50 kV, 70 kV, 100 kV, 130 kV, 250 kV or any other such value, in various implementations. In many implementations, the electrode may comprise a conductive material, such as aluminum, although other materials and shapes may be utilized.

Exterior insulator 212: A sufficiently insulative non-conductive material layer of at least ⅛" or more thickness. In many implementations, the exterior insulator 212 may be perforated as shown to allow air to pass between the air gap provided by frame 206 and a chamber of the container bounded by reactor 104. In many implementations, a portion of the insulator 212 may be solid, e.g. to support an electrode 210 and associated wiring as shown.

Electrodes 202, 210 may sometimes be referred to as a high voltage electrode and ground electrode. For example, electrode 202 may comprise a ground electrode, and electrode 210 may comprise a high voltage electrode. A high voltage generator (not illustrated) may be attached to the electrodes 202, 210. The various layers of the reactor 104 may be attached to each other via non-conductive bolts or screws, adhesive epoxies, or other such fasteners. The edges of the reactor may be substantially sealed, excepting open portion(s) of frame 206, to prevent gas leakage.

Figure 2B:
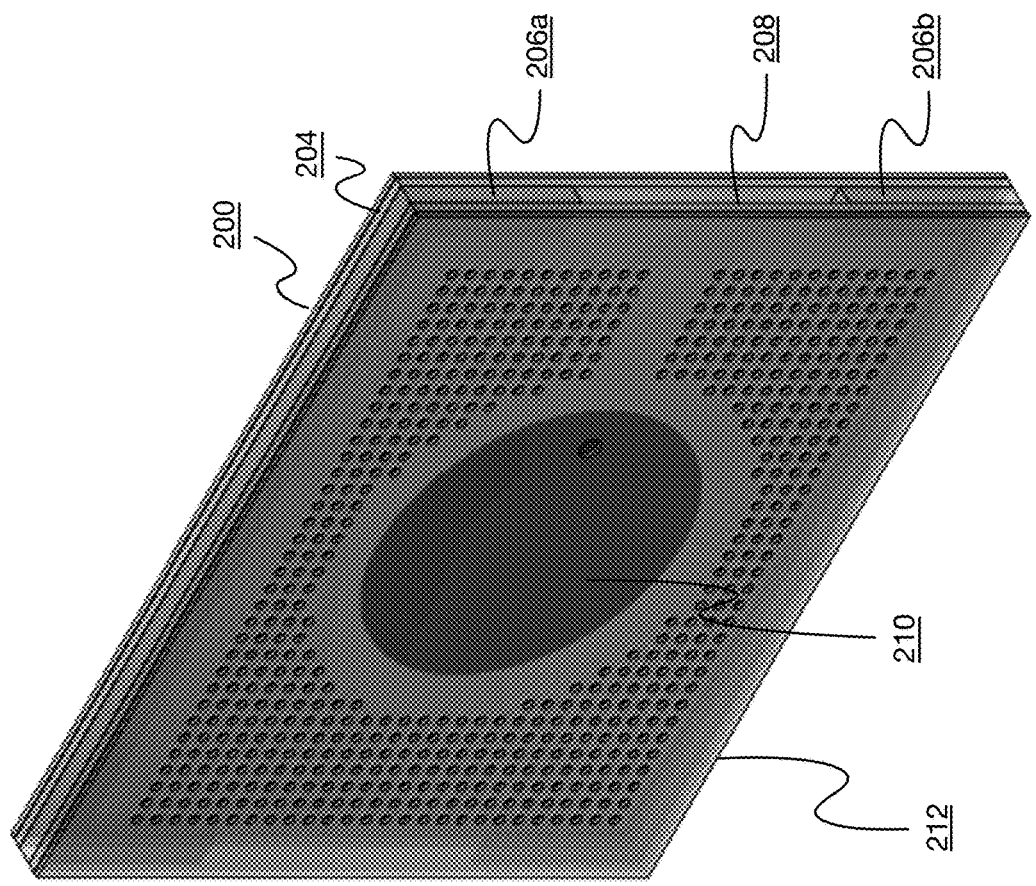
FIG. 2B is an isometric view of the cold plasma reactor of FIG. 2A, according to some implementations.

FIG. 2B is an isometric view of the assembled cold plasma reactor 104 of FIG. 2A, according to some implementations. As shown, when assembled, the layers 200-212 are substantially adjacent, preventing gas leakage other than via the gap(s) formed by frames 206a-206b and the perforations (e.g. in layers 208, 212).

Figures 2D, 2E:
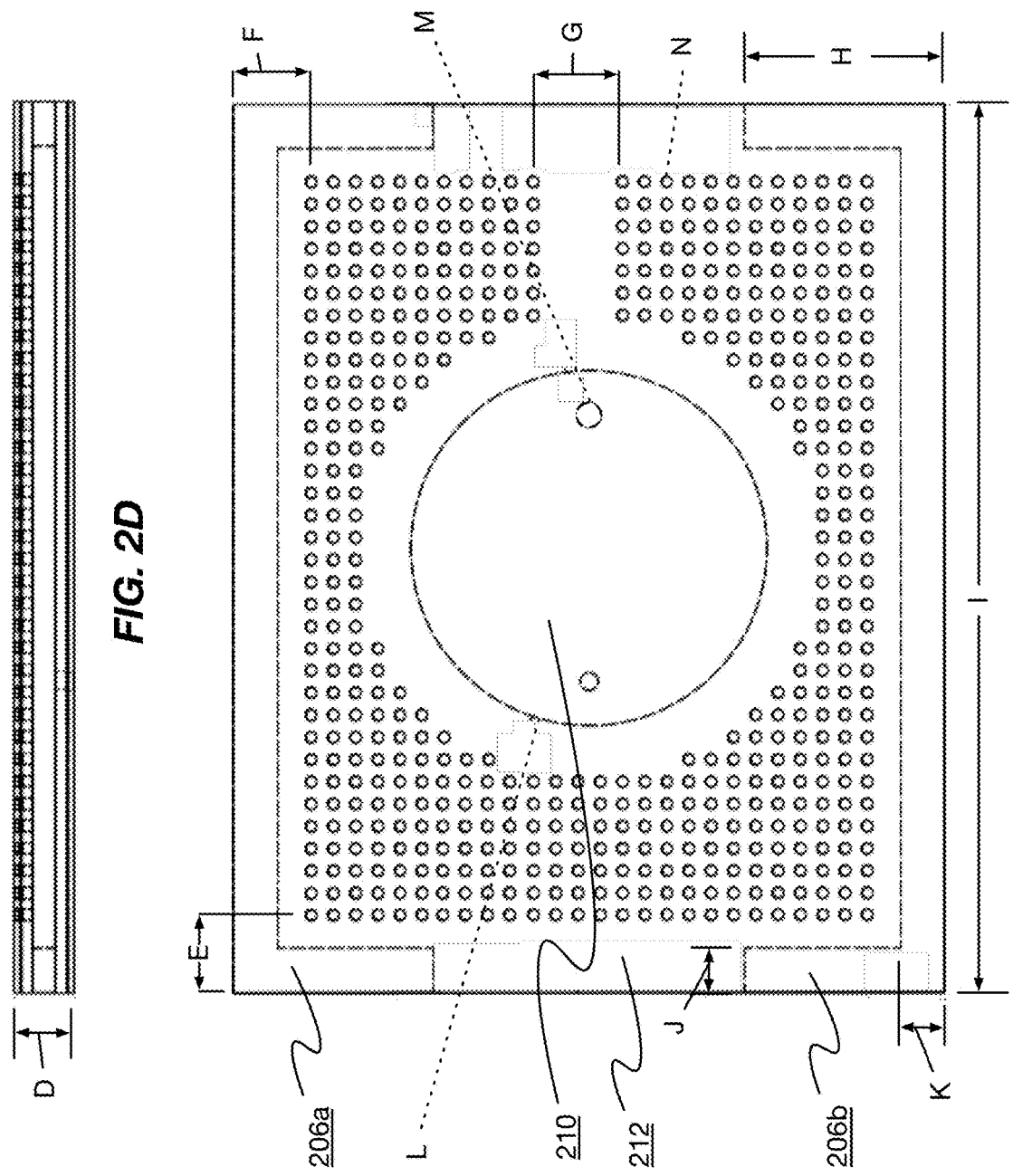
FIG. 2D is a top view of the cold plasma reactor of FIG. 2A, according to some implementations.
FIG. 2E is a front view of the cold plasma reactor of FIG. 2A, according to some implementations.
Figure 2C:
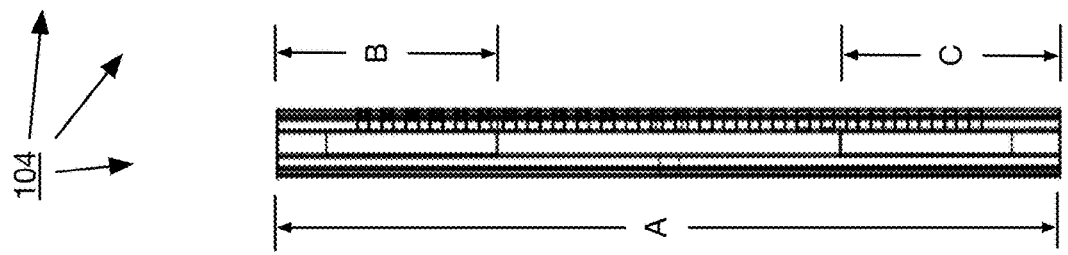
FIG. 2C is a side view of the cold plasma reactor of FIG. 2A, according to some implementations.

FIGS. 2C-2E are a side view, top view, and front view, respectively, of the cold plasma reactor 104 of FIG. 2A, according to some implementations. In the front view of FIG. 2E, locations of frames 206a-206b are shown in dashed line, as is the location of electrode 210. Various dimensions may be utilized for the reactor 104, allowing scaling to smaller or larger sizes depending on the container to be used. In one such implementation, the dimensions include:

| Dimension | Value |
| --- | --- |
| A | 16.00" |
| B | 4.50" |
| C | 4.50" |
| D | 1.35" |
| E | 1.75" |
| F | 1.75" |
| G | 2.00" |
| H | 4.50" |
| I | 20.00" |
| J | 1.00" |
| K | 1.00" |
| L | Ø8.00" |
| M | Ø0.53" |
| N | Ø0.25" |

Figure 2F:
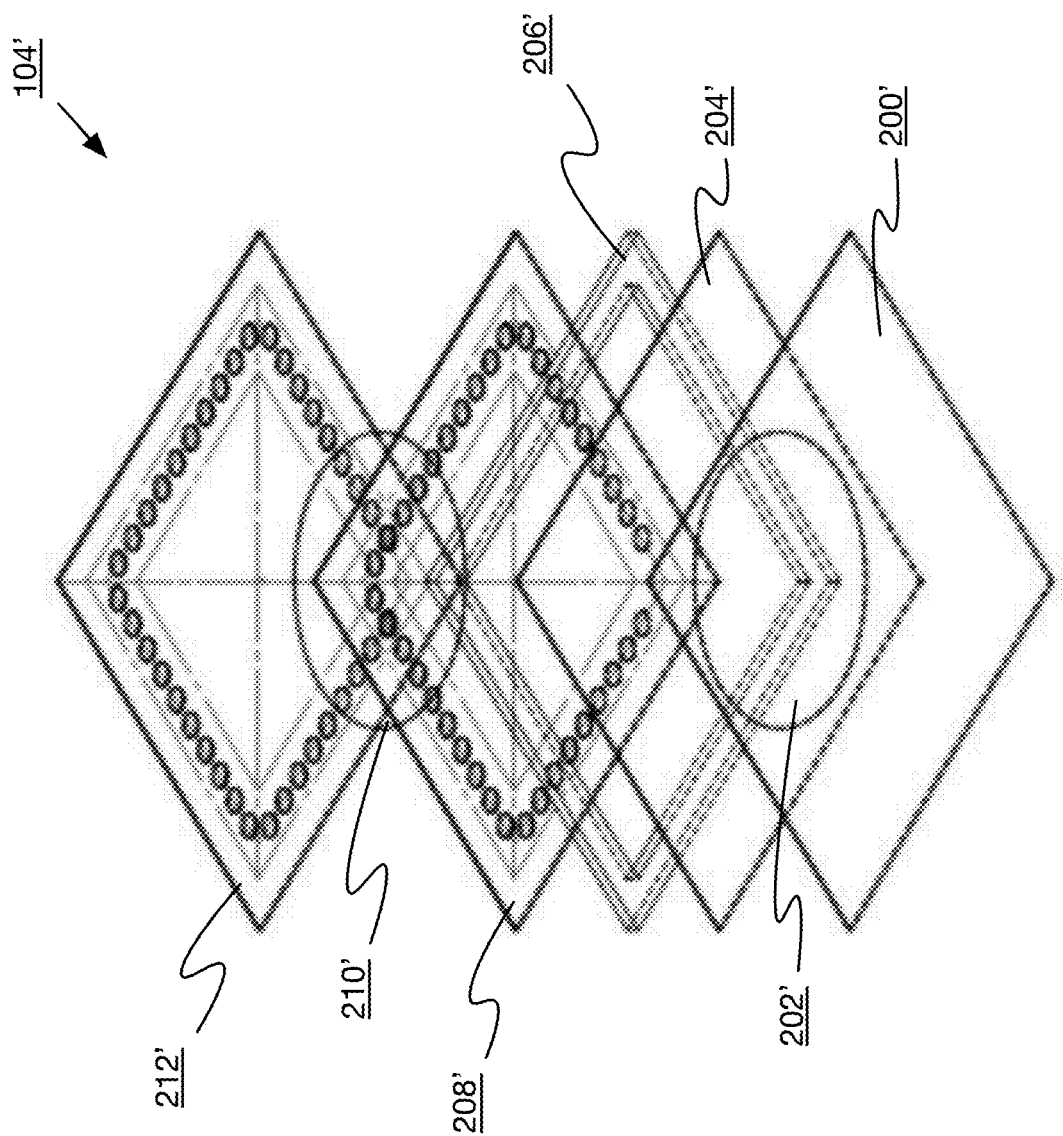
FIG. 2F is an exploded view of another implementation of a cold plasma reactor.

The dimensions may be scaled to larger or smaller values while maintaining the same ratios, in many implementations. In other implementations, other sizes may be used (e.g. the reactor may be square, or have a different aspect ratio). For example, FIG. 2F is an exploded view of another implementation of a cold plasma reactor 104'. The reactor 104' includes layers 200', 202', 204', 206', 208', 210', and 212', similar to those discussed above, but has a square aspect ratio (e.g. 20" by 20", in one implementation), and has a different configuration of perforations in layers 208', 212' (e.g. 1" diameter holes, in one implementation).

The plasma generation device may also be integrated into a 'reactor' or environment which is not a container. The generator (or multiple generators) may be integrated in an open system which is not hermetically sealed or closed, but rather controls the specific direction of gas flow, velocity and diffusion of gas. In effect, the generator may be integrated into any device or system which can control the movement of gas and its contact with food products.

Figure 3:
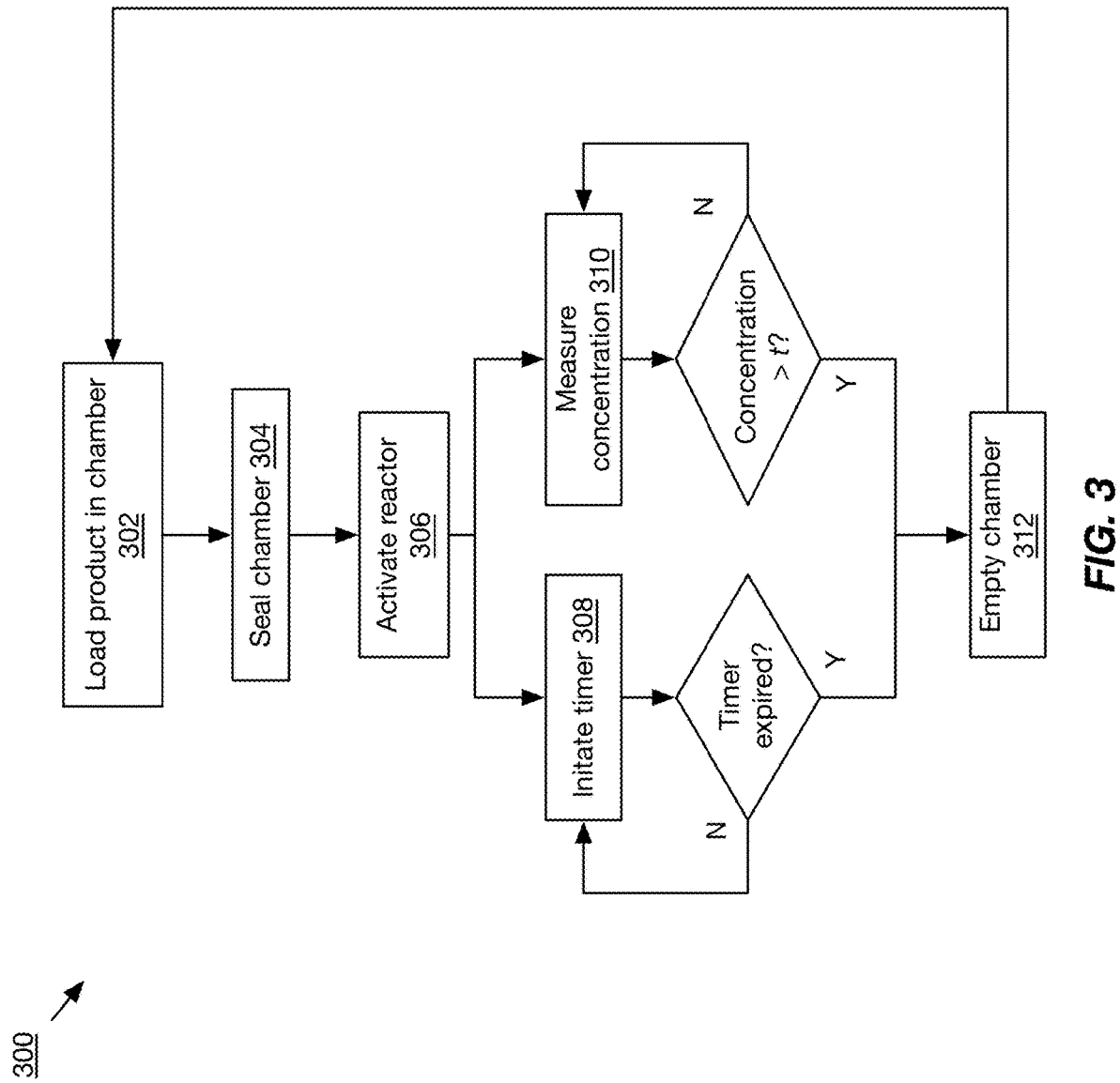
FIG. 3 is a flow chart of an implementation of a method for treating product.

FIG. 3 is a flow chart of an implementation of a method 300 for treating product. At step 302, a product may be loaded into an interior chamber of a container, with one or more cold plasma reactors on or forming walls of the container. The product may be any type of product, such as a medical implement, industrial implement, or food product, such as nuts, grains, or other such food products. The product need not be placed in any further interior container (e.g. vacuum sealed pouch or other such container) in many implementations.

At step 304, the chamber may be hermetically sealed. Sealing the chamber may comprise closing a door, hatch, or other such opening through which product is loaded. The chamber may include a gasket or other feature to prevent the escape of plasma and RGS. The chamber may contain a gas, such as atmospheric air at room temperature. The chamber may also be open or allow for the free flow of product using conveyors or a gravity fed system. RGSs in an open system may be contained by air curtains, controlled diffusion out of the system by the product under treatment or simply by calculating the rate of diffusion of each specific gas species.

At step 306, the reactor(s) may be activated by applying a high voltage between the electrodes. The high voltage may be generated by an external power supply, and may be at 10 kV, 20 kV, 30 kV, 50 kV, 70 kV, 100 kV, or any other such value sufficient to generate a plasma and RGS.

In some implementations, at step 308, a timer may be initiated and may run for a predetermined period of time to allow the RGS generated by the reactors to diffuse through the chamber and product. The period of time may be predetermined based on the size of the chamber, the RGS generation rate, the density of the product, etc. In some implementations, the time may be 10 minutes, 20 minutes, 30 minutes, one hour, or any other such value.

In some other implementations, at step 310, a concentration of the RGS or a particular gas (e.g. $O_3$) within the chamber may be measured until it has reached a concentration above a predetermined threshold (e.g. above 7000 parts per million by volume (ppmv)). Measuring the gas concentration may be more accurate than using time in some implementations in which diffusion rate through the product may be unknown or highly variable due to packing. In some implementations, both a timer and gas concentration may be measured.

Upon the timer expiring and/or the concentration exceeding the threshold, at step 312, the chamber may be emptied of product. The reactors may be deactivated, and the chamber evacuated of RGS and plasma (e.g. via a fan or vacuum). In some implementations, a hatch or port may be opened in the chamber to allow the product to fall into an output bin. The hatch may be closed once the chamber is emptied, and the process may be repeat for another batch of product.

In another implementation, step 306 may be performed before step 302. For example, in some implementations, product may be loaded into a first pre-treatment bin that may be hermetically sealed. The reactors may be activated and RGS generated. The product may then be allowed to enter the chamber with the RGS. This may speed diffusion of the RGS throughout the product and may accelerate treatment of the product, in some implementations.

Figure 4:
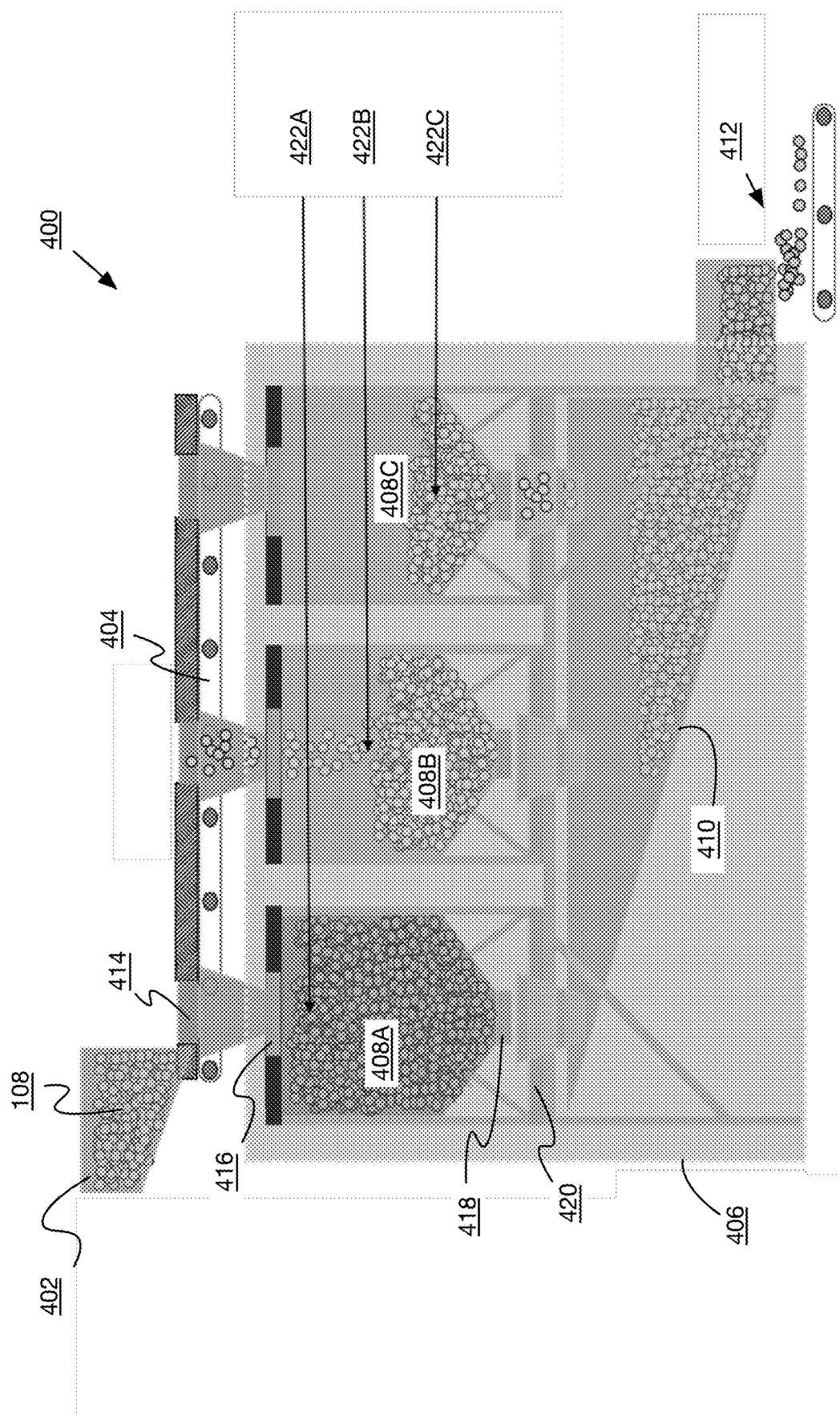
FIG. 4 is an illustration of a system for treating product, according to some implementations.

FIG. 4 is an illustration of a system 400 for treating product, according to some implementations. Product 108 may be loaded via a hopper or pre-treatment bin 402 and allowed to flow onto a loading conveyor 404. The conveyor may transport product into one or more treatment bins 408A-408C within a hermetically sealed enclosure 406, via conveyor gates 414 corresponding to each bin. Once full (which may be determined via a bin scale 420 integrated into each bin 408A-408C, in some implementations), the bin may be sealed via a bin seal 416. Each bin 408A-408C may comprise one or more reactors 104, such as on side walls of the bin. The product may be treated within the bin as discussed above, and once complete, may be discharged via discharge gates 418 into an off-loading bin 410, and thence to an output conveyor 412. By using three (or more) bins 408A-408C as shown, one bin may be undergoing treatment (e.g. at step 422A) while a second bin is loading in preparation for treatment (e.g. at step 422B) and a third bin is emptying after treatment (e.g. at step 422C). This may allow for throughput of hundreds of kilograms or several metric tons of product per hour or more. In some implementations, RGS products generated by reactors in one bin may be evacuated into a second bin (e.g. from a bin finishing treatment into one loaded and ready for treatment), accelerating the diffusion process.

Figure 5:
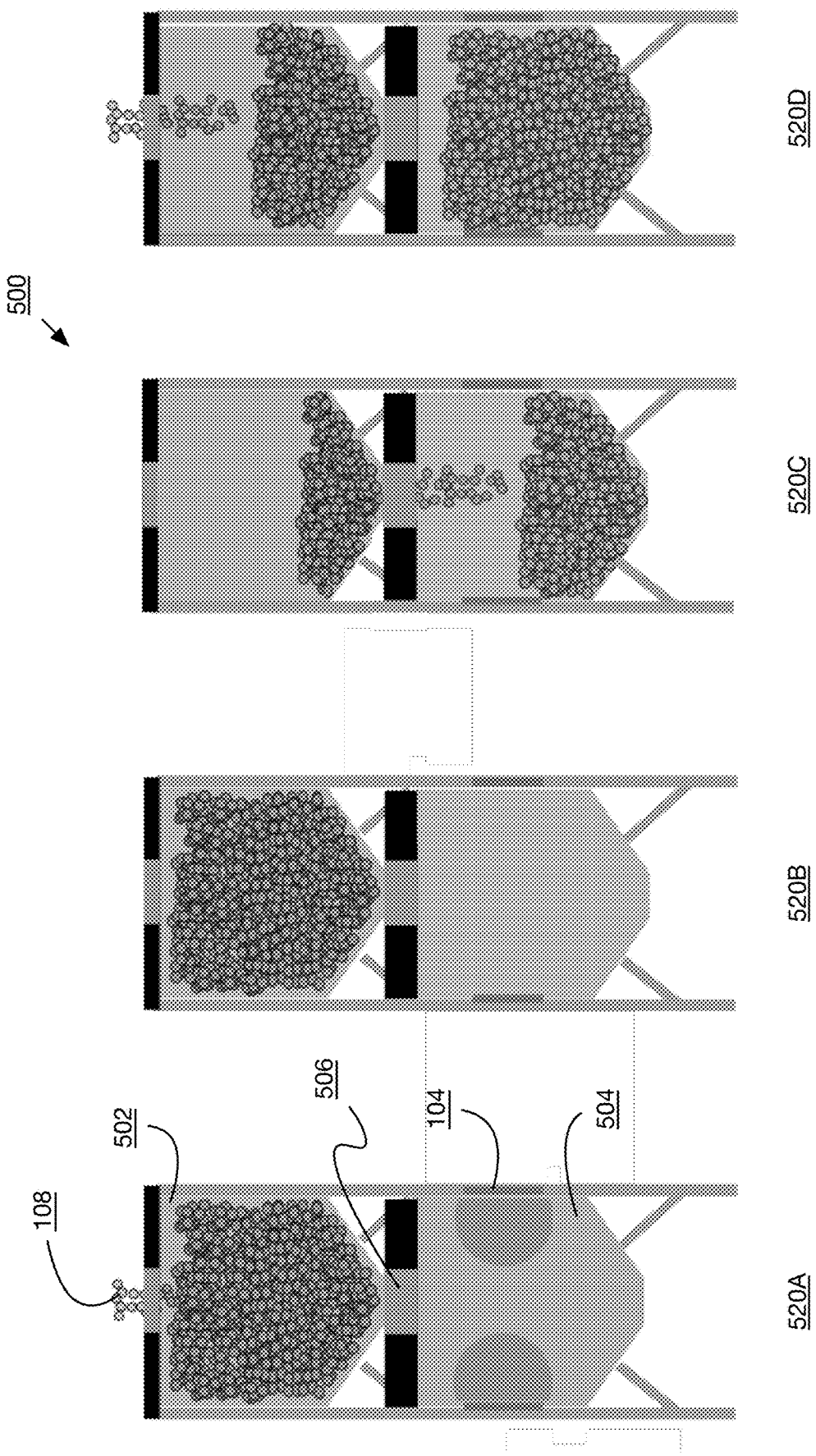
FIG. 5 is an illustration of another system for treating product, according to some implementations.

FIG. 5 is an illustration of another system 500 for treating product, according to some implementations. A loading bin 502 may be stacked on top of a treatment bin 502 comprising one or more reactors 104, and accessed via a seal or gate 506. At step 520A, product 108 may be loaded into loading bin 502, and reactors 104 may be activated to generate RGS within the treatment bin 504. Once loaded, the loading bin may be closed at step 520B. At step 520C, the gate 506 may be opened to allow product 108 to flow into the treatment bin 504. In some implementations, the product itself may act as a hermetic seal during this process, preventing the RGS from escaping into the loading bin. Once the loading bin is empty, at step 520D, the gate 506 may be closed and the product may undergo treatment within the treatment bin. Additional product may be loaded into the loading bin at this time, increasing efficiency. By activating the reactors at step 520A, this may allow the RGS to diffuse through the empty chamber in advance, creating a more homogenous distribution within the chamber in a shorter period of time. This may allow for faster treatment of the product at step 520C.

Figure 6A:
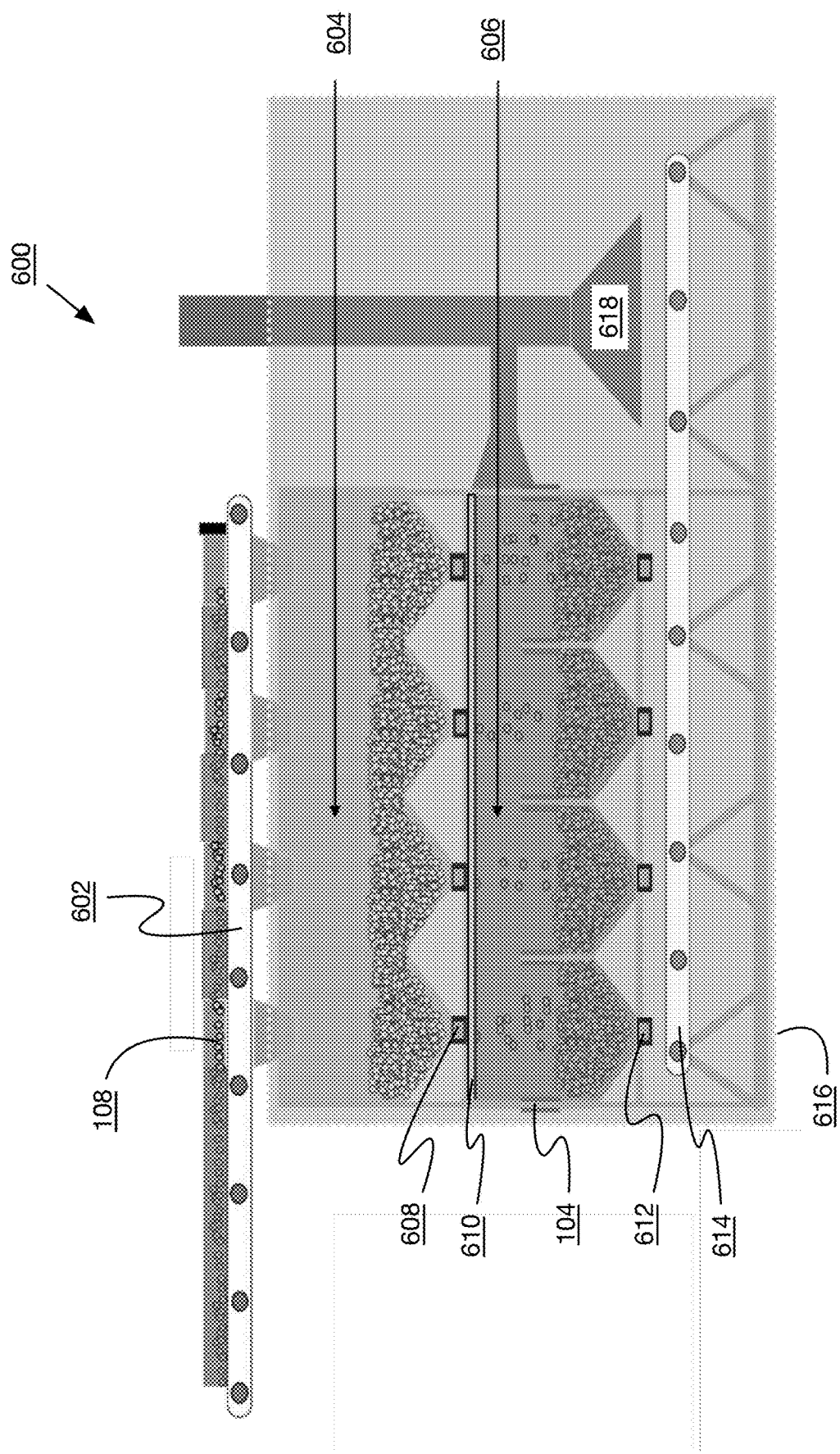
FIG. 6A is an illustration of still another system for treating product, according to some implementations.

FIG. 6A is an illustration of still another system 600 for treating product, according to some implementations. Multiple sections of the system of FIG. 5 may be joined, forming a large pre-treatment bin 604 and large treatment bin 606. These components may be modular, allowing for easy scalability. As discussed above, product 108 may be transported via a loading conveyor to loading hatches in the pre-treatment bin sections. Once a predetermined amount of the product has been loaded (e.g. as determined by a bin scale 610, in some implementations), the product may pass through gates 608 into treatment bins 606 with integrated reactors 104. The gates may be closed and the product may be treated while the pre-treatment bins are reloaded for subsequent treatment rounds. Once treatment is complete, the treatment bins may be emptied via bin seals 612 onto an output conveyor 614. In some implementations, the pre-treatment and treatment bin sections may be enclosed in a hermetically sealed chamber 616. This chamber may also include an exhaust fan, in some implementations, for removing RGS products after treatment, and/or for maintaining a flow of gases through the products under treatment.

Figure 6B:
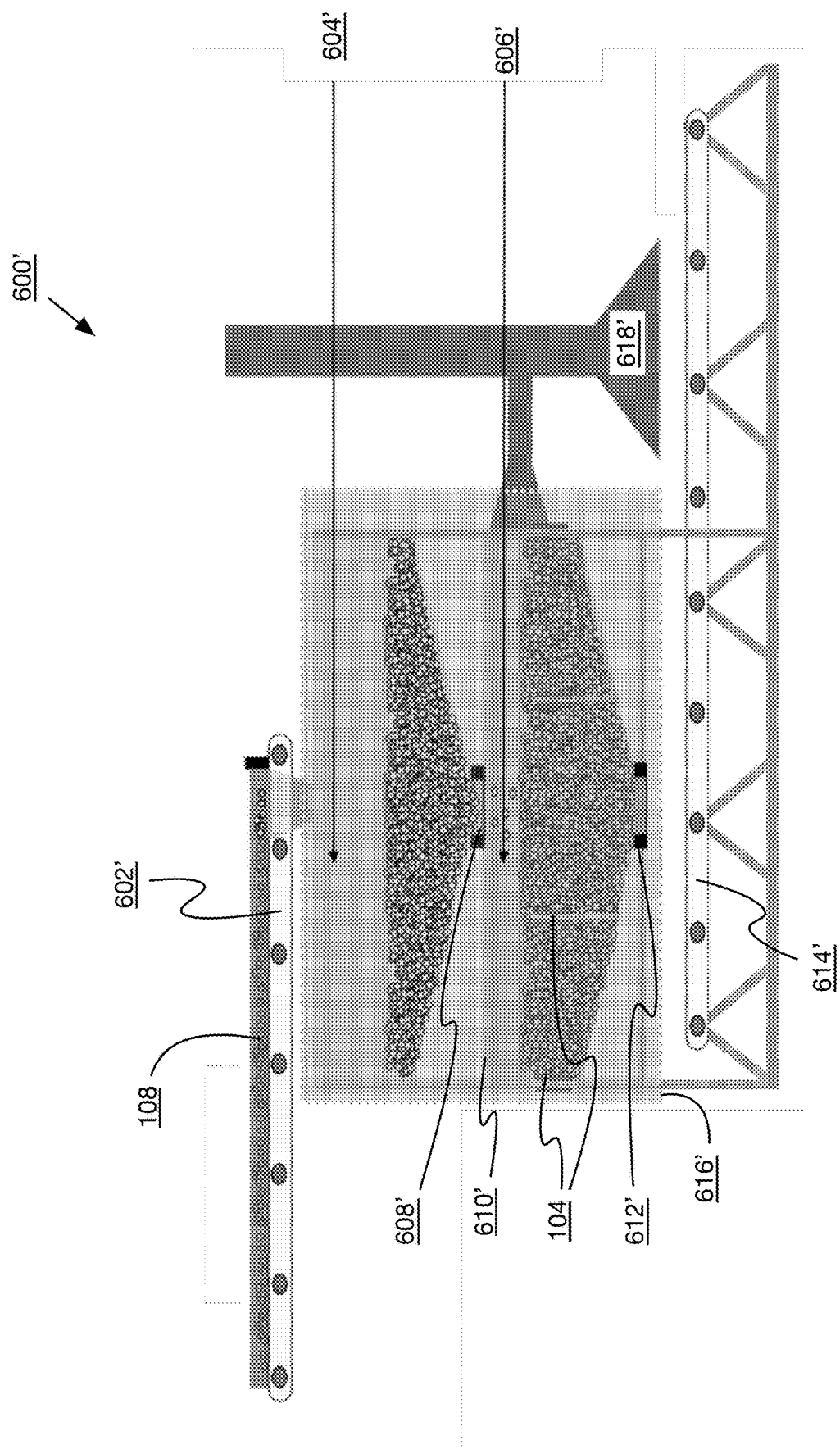
FIG. 6B is an illustration of another implementation of the system for treating product of FIG. 6A.

FIG. 6B is an illustration of another implementation of the system 600' for treating product of FIG. 6A, in which a single larger pre-treatment bin 604' and treatment bin 606' are utilized rather than modular sections. While such implementations may be less flexible in terms of reconfiguration for scaling, they may be less expensive to manufacture. In some implementations, additional reactors 104 may be installed within the treatment chamber 606' (e.g. on internal risers that do not extend fully to the top and/or sides of the bin, allowing product to pass around or over the reactors 104 during filling). This may allow for faster diffusion of RGS through the product under treatment compared to only having reactors on the sides of the bin (which may be very large, in some implementations).

FIGS. 7A and 7B are diagrams illustrating implementations of systems without interior reactive gas species generation and with interior reactive gas species generation, respectively; In some implementations, treatment systems may include multiple RGS generation cells 104 inside of a container or throughout a continuous flow processing point. This interior generation provides a continuous and sustained concentration of RGSs. For example, FIG. 7A illustrates an implementation of a system 700A with a single plasma reactor 104 on an exterior wall of a chamber for treating product 108. The generated RGS products diffuse through the interior of the chamber with a highest concentration 702A near the plasma reactor 104 (e.g. 5,000 ppm); a moderate concentration 702B farther from the plasma reactor 104 (e.g. 2,500 ppm); and a lower concentration 702C still farther from the plasma reactor 104 (e.g. less than 1,000 ppm). Such implementations may require longer treatment times to ensure that the RGS products diffuse throughout the container, or may result in a non-homogenous treatment of product.

Conversely, FIG. 7B illustrates an implementation of a system 700B with a plurality of plasma reactors 104 positioned within the chamber. In many implementations, the interior plasma reactors 104 may not extend to all sides of the container, such that product 108 and RGS products may flow around, above, and/or below each reactor 104 (for example, interior reactors may be mounted on small or thin standoffs or risers, in some implementations, with open space below, to the side of, and above each reactor). These interior generation points provide the unique ability to sustain RGS concentration without requiring transporting or diffusing of gases from one location to another (although some implementations may further incorporate fans or other implements to diffuse the gases, in addition to interior generation points). Such implementations may ensure that all products treated within the system have a more homogeneous treatment rather than the product closest to the RGS generation points contacting larger volumes of gas or having longer exposure periods relative to the product further from the generation points.

In some implementations, the treatment of products using the device may also be within an open system. This may occur using a mechanical structure which controls the flow of product but is not hermetically sealed or has specific control over the entry and exit of the product. For example, FIG. 8 is a diagram of an implementation of a gravity-fed system 800 for treating product 108. A column 802 may comprise a plurality of baffles 806 deployed within a treatment region 804. The baffles may extend across the treatment region 804 with openings to allow a limited amount of product 108 to flow through to a next baffle over time. This may stall the flow of product 108 through the system 800, resulting in the product spending some amount of time (e.g. 10 minutes) between each set of baffles, resulting in a total treatment time as a multiple of the baffles (e.g. 50 minutes for 5 baffles). In some implementations, plasma reactors may be positioned on the sides of the chamber of the treatment region 804. In other implementations, plasma reactors may be deployed within baffles 806. For example, each baffle 806 may include a solid top surface to support product above the baffle; an integrated plasma reactor; and a perforated, slotted, or open bottom surface to allow RGS products produced by the reactor to diffuse into the next chamber between the baffle and a subsequent (e.g. lower) baffle 806. Advantageously, such implementations may not require control valves or hatches at the top and bottom of the system 800 to contain RGS products, as the product filling openings within each baffle layer may provide a hermetic seal as shown.

Figure 9:
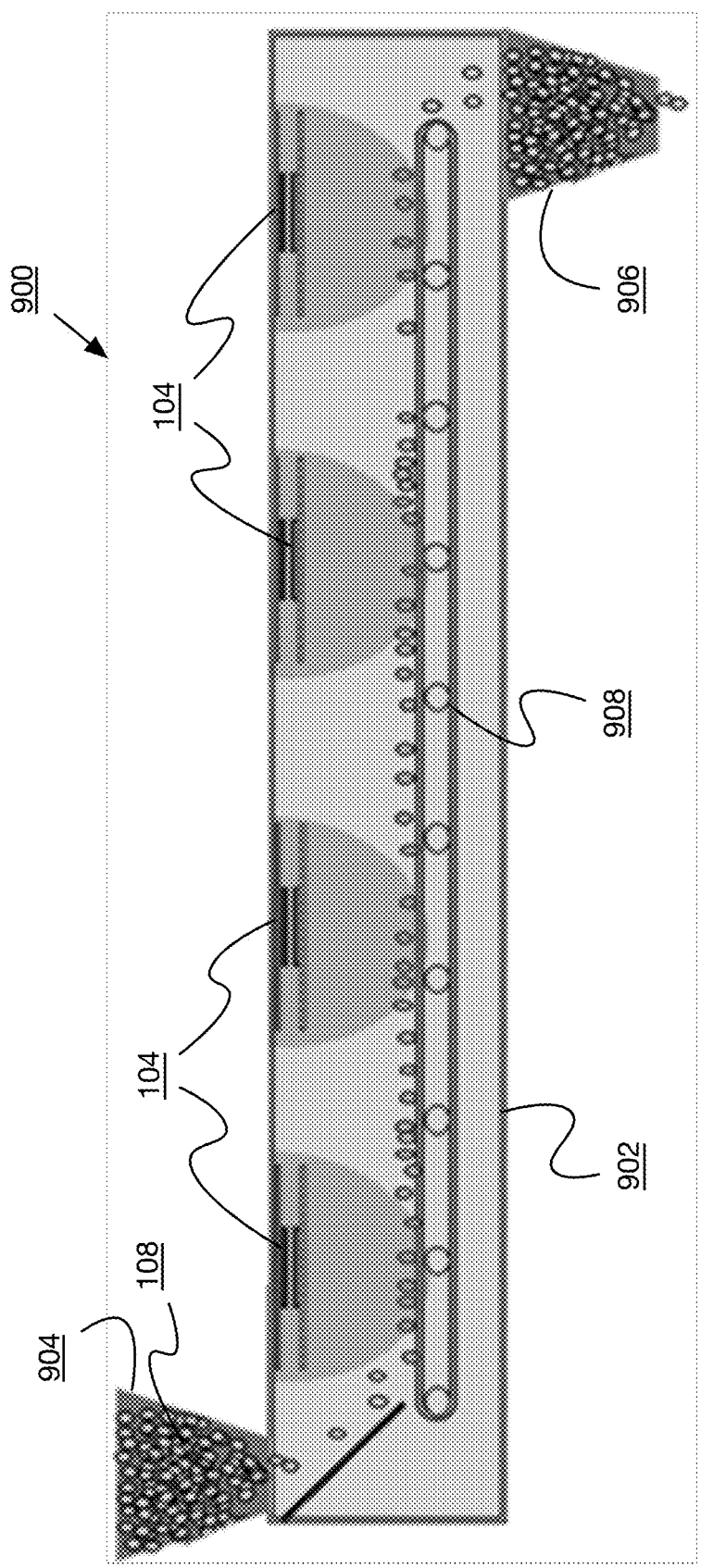
FIG. 9 is a diagram of an implementation of a conveyor system for treating product.

In another implementation, a conveyor may be placed within a container which contains the gases generators using the compaction of the product on either end of the system to provide a hermetic seal, or an air curtain which ensures all gases treating the products do not dissipate or move away from the product. FIG. 9 is a diagram of such an implementation of a conveyor system 900 for treating product. A container 902 may include a conveyor 908 for transporting product 108 under treatment past one or more plasma generators 104, which may be deployed on the top of the container in some implementations, and/or on the sides of the container or beneath the conveyor 908. In some implementations, entry hopper 904 and exit hopper 906 may limit the flow of product through the container such that collected product 108 in each hopper 904, 906 provides a hermetic seal for RGS products within the container.

In some implementations, a particular product-to-gas ratio may need to be maintained within treatment containers. FIG. 10 is an illustration of volume capacity during treatment, according to some implementations. In some implementations, the product being treated may only occupy between approximately 5-90% of the total volume of space within the container or treatment device, or the plasma generators may not be able to sustain generation of the necessary reactive gases in sufficient volumes or with sufficient diffusion rates. For example, at left, FIG. 10 illustrates a container 1000A having a large gas volume 1002A relative to an amount of product 108; while at right, FIG. 10 illustrates a container 1000B having a small gas volume 1002B relative to an amount of product 108. In some implementations, the system at right may not be able to properly generate sufficient RGS products and treat the product. Various methods may be used to control the amount of product under treatment, including hatches, doors, valves, or hoppers or similar structures having size-limited openings into the treatment container to limit the flow of product.

Figure 11:
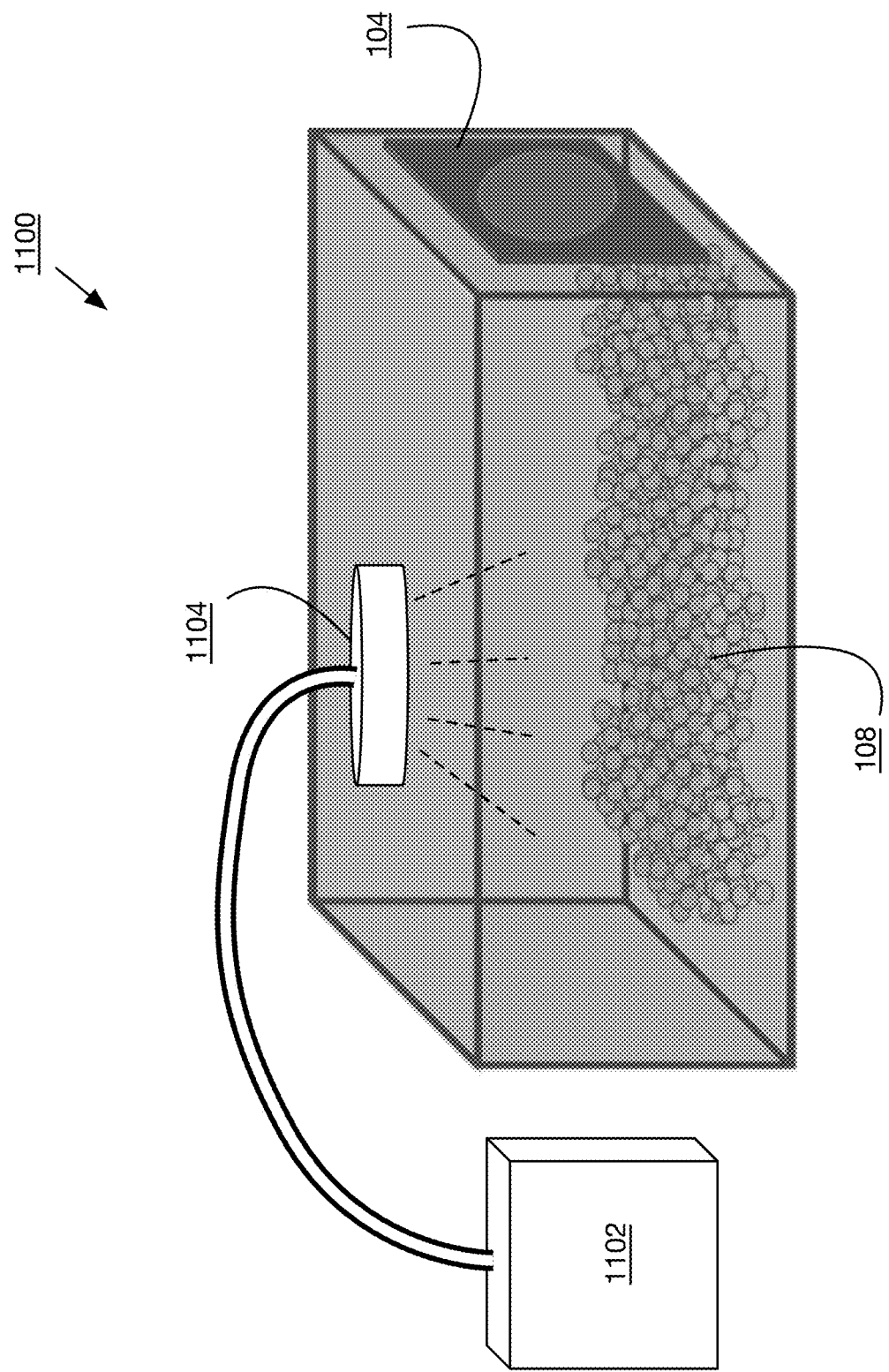
FIG. 11 is an illustration of a system utilizing an exterior feed gas supply, according to some implementations.

In some implementations, rather than using ambient air as a pre-reaction gas, implementations of the systems and methods discussed herein may use ozone ($O_3$) as a feed gas or substitute for ambient air. In these high voltage conditions, ozone serves as a catalyst for other reactive gas species such as nitrates, nitrites and peroxides used for decontamination and sterilization of food products. FIG. 11 is an illustration of a system 1100 utilizing an exterior feed gas supply 1102, according to some implementations. Gas supply 1102 may comprise any suitable source of ozone, such as a pressured gas tank or an ozone generator, and may be connected via a tube or hose to a diffuser 1104 or opening into the treatment container.

Figure 12A:
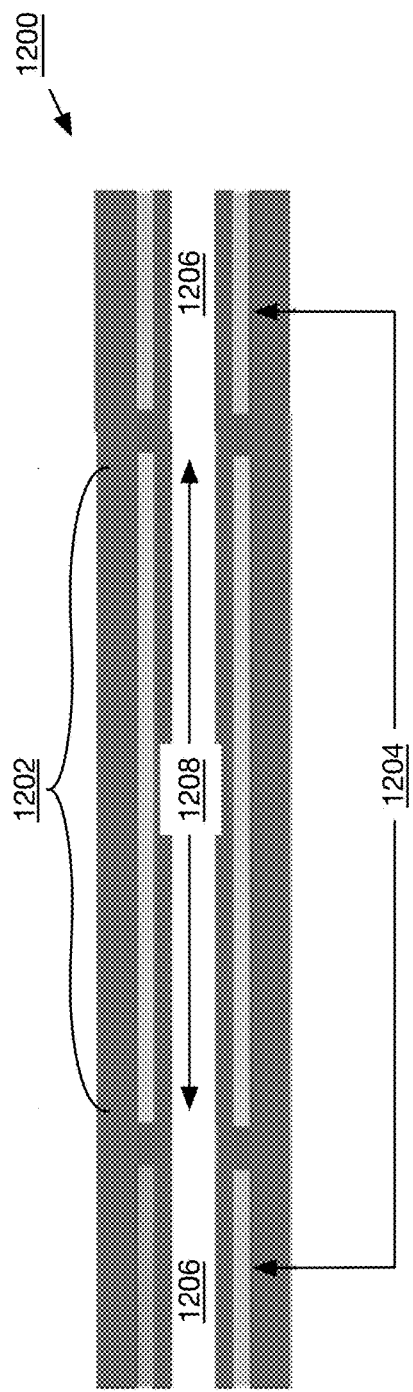
FIG. 12A is a side view of an implementation of a cold plasma reactor, according to some implementations.

FIG. 12A is a side view of another implementation of a cold plasma reactor 1200, according to some implementations. Similar to reactor 104, cold plasma reactor 1200 may also be used for in situ ozone generation in the event ozone feed gas is not required or available. A portion of reactor 1200 may include a low voltage dielectric barrier system. For example, outer portions 1204 may comprise a pair (or pairs) of electrodes in the upper and lower portions of reactor 1200 to which lower voltages (e.g. 2-10 kV in many implementations, though higher voltages may be possible in some instances) are provided to generate ozone in regions 1206 from oxygen in ambient air or feed oxygen or oxygen mixtures; center portion 1202 may comprise a pair (or pairs) of electrodes in the upper and lower portions of reactor 1200 to which higher voltages (10-120 kV in many implementations, or higher, as discussed above) are provided to generate RGS products 1208 from the generated ozone. Such configurations may reduce energy consumption otherwise required to $1^{st}$ convert oxygen to ozone (the catalyst), then subsequently generate the more stable RGSs.

In some implementations, the reactor 1200 may comprise a multi-layered plasma generation dielectric barrier discharge (DBD) system which uses different geometries at different intervals to produce ozone in some areas and different RGSs in other locations. In some such implementations, small generation points may ensure that 100% of the treatment environment has a sustained gradient of RGSs (homogenous treatment).

Figure 12B:
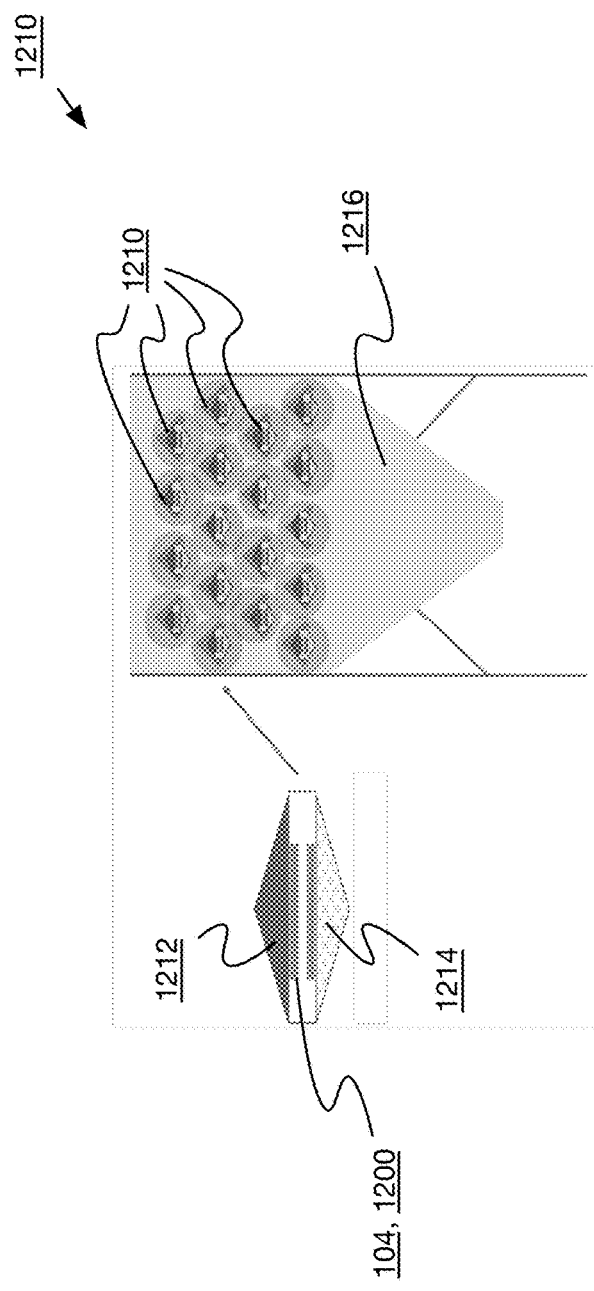
FIG. 12B is a cross-section illustration of an implementation of a system for treating product, according to some implementations.

In some implementations and as discussed above, a reactor 1200, 104 may be enclosed in a barrier or baffle, or be equipped with a shield or cover, to be deployed within a container. FIG. 12B is a cross-section illustration of an implementation of a system 1210 for treating product, according to some implementations. A reactor 104, 1200 may be attached to or comprise a solid upper cover or top portion 1212; and a perforated, slotted, or open bottom portion 1214 to allow RGS products to flow through. A plurality of such shielded reactors may be deployed within a container 1216, such as in baffles or columns extending across the container (while allowing product to pass between neighboring reactors). Such implementations may allow for multiple points of RGS generation within the container 1216, speeding diffusion and treatment of product.

Figure 13:
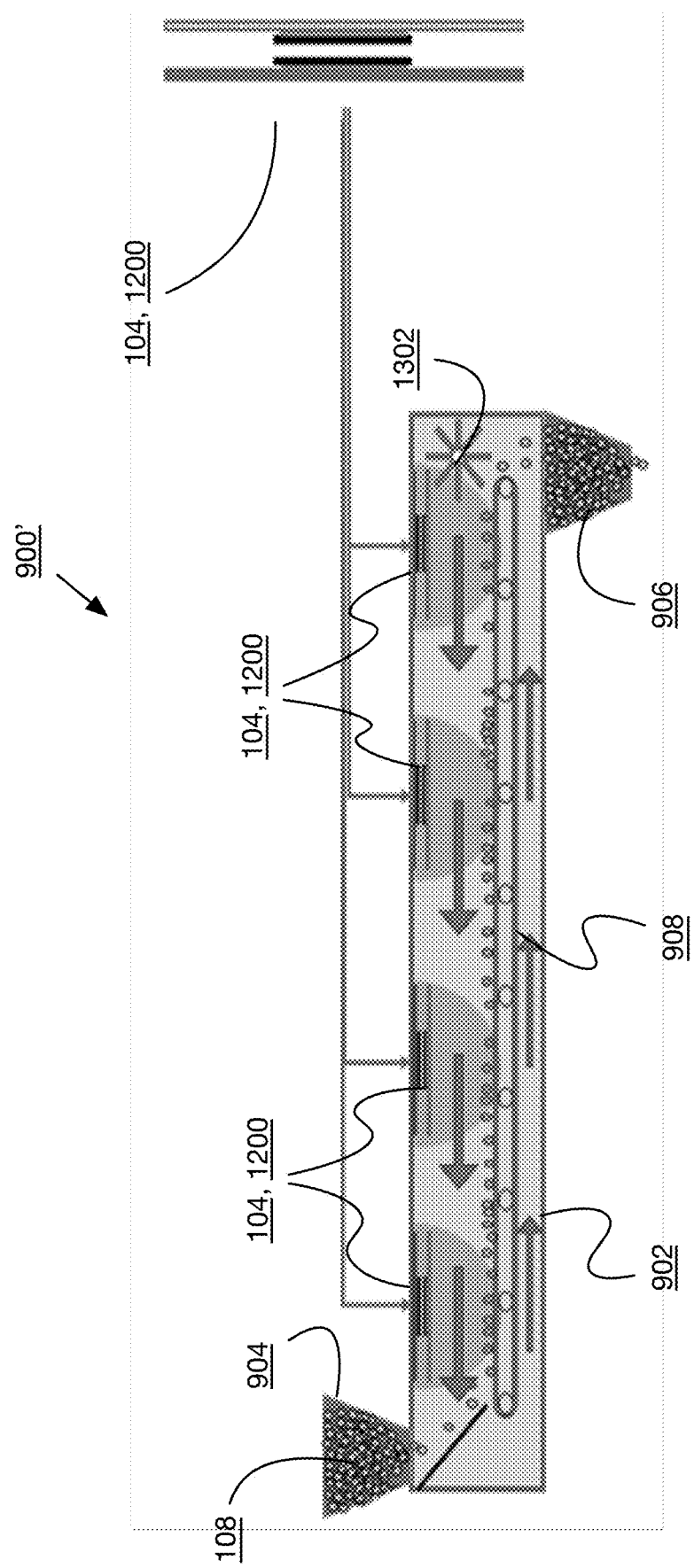
FIG. 13 is an illustration of an implementation of the system of FIG. 9 utilizing a reactive gas species dispersion fan.

Fans or blowers may also be used to diffuse RGS products through a treatment area. FIG. 13 is an illustration of another implementation 900' of the system of FIG. 9 utilizing an RGS dispersion fan 1302. One or more reactors 104, 1200 may be deployed within the container 902 (e.g. on side walls, a top surface, and/or bottom surface). As a conveyor 908 moves product 108 through the container 902, dispersion fan 1302 blows RGS products generated by reactors 104, 1200 through the container, ensuring a homogenous treatment environment.

An implementation of the systems and methods discussed herein was tested for efficacy using whole roasted peanuts artificially contaminated with approximately 250 ppb of aflatoxin B 1. 5 mg pure aflatoxin was dissolved with methanol, and 1 ml of aflatoxin solution was applied to each sample of 200 g peanuts. The samples were placed in a hood for at least 4 hours to allow the solvent methanol to fully evaporate.

The testing apparatus comprised a chamber with a ½" electrode gap and two ⅛" polypropylene dielectric barriers. The electrodes comprised 15 cm diameter spun aluminum disks, driven by an external power supply to 50 kV and 70 kV for the tests. The chamber was 50 cm×38 cm×2.5 cm, filled with approximately 4750 ml of room temperature air at 40% humidity. The overall dimensions of the apparatus were 14.5 inches×11.4 inches×0.75 inches. The test product was treated for one hour in plasma generated in room air (at 21 degrees Celsius, and 100 kPa pressure) in an indirect treatment at both 50 kV and 70 kV. Power consumption for the tests were 73.3 W and 135 W, respectively. Optical absorption spectroscopy was used to measure gas concentrations within the chamber during activation of the reactor, and aflatoxin and peroxide values were measured after treatment and compared to a control sample.

Figure 14A:
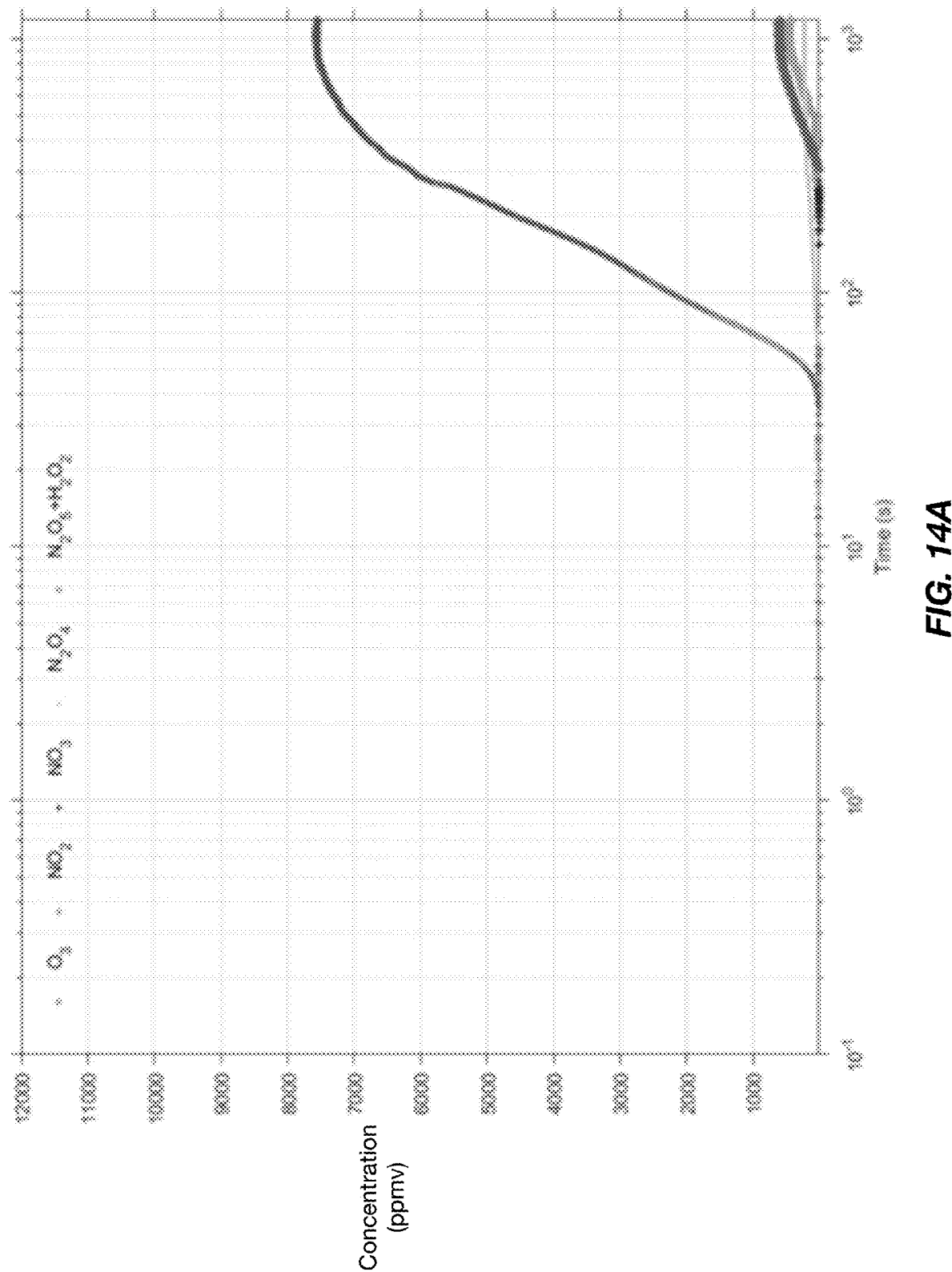
FIG. 14A is a graph illustrating kinetics of gas species generated during a 50 kilovolt (kV) treatment for 20 minutes by one implementation of a system for treating product.
Figure 14B:
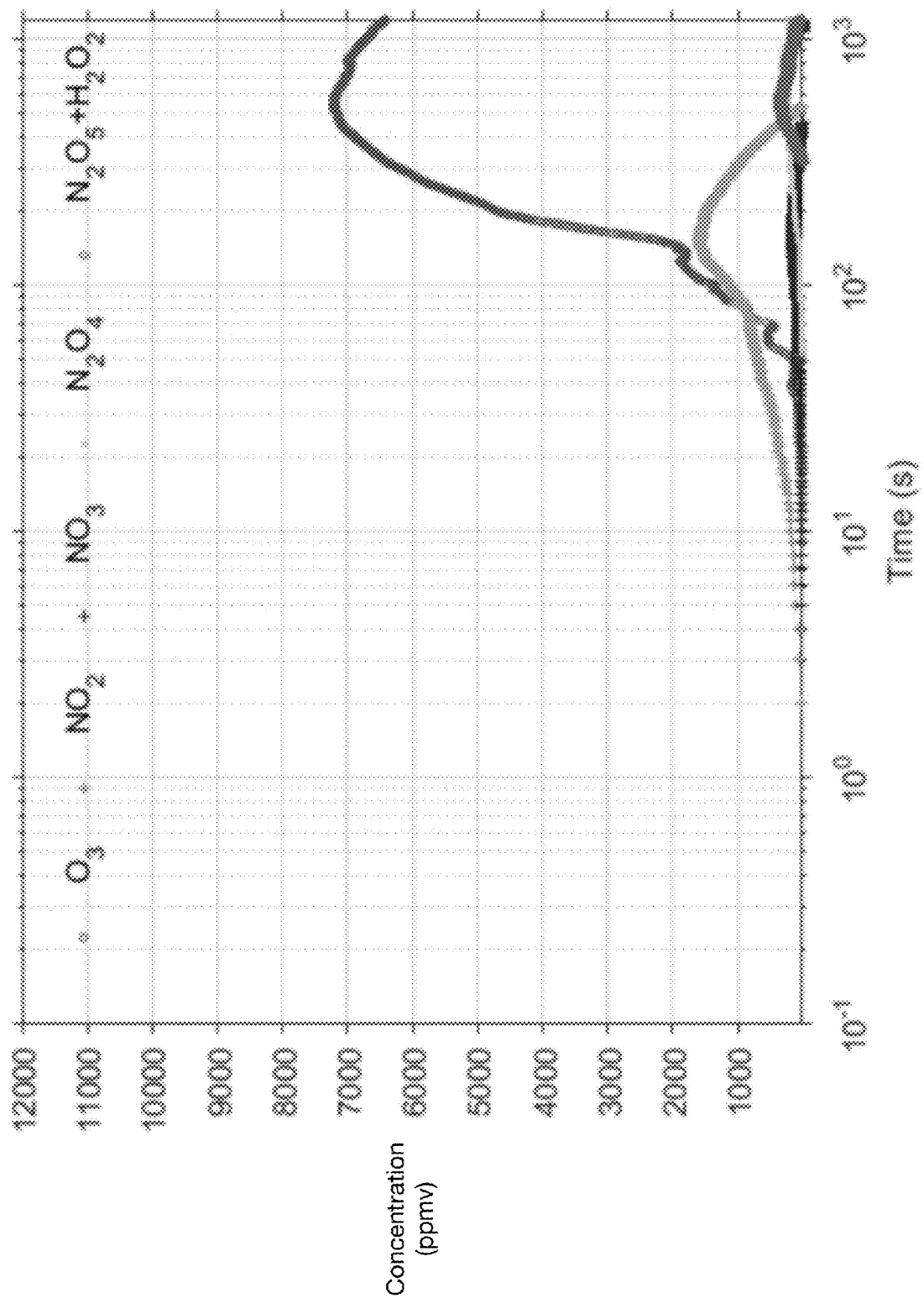
FIG. 14B is a graph illustrating kinetics of gas species generated during a 70 kilovolt (kV) treatment for 20 minutes by one implementation of a system for treating product.

FIG. 14A is a graph illustrating kinetics of gas species generated during a 50 kV treatment for 20 minutes during the test, measured via optical absorption spectroscopy via two fiber optic probes within the chamber with a path length of 21 mm, at a sample rating of 4 scans per second, averaged over one second. Similarly, FIG. 14B is a graph illustrating kinetics of gas species generated during a 70 kV treatment for 20 minutes during the test. Running either at 50 or 70 kV, the concentration of gas species (ozone and nitrogen species) generated by the reactors follow a similar trend: firstly, rapid increase with treatment time, and then gradually decreasing after the gas species reached its peak. The decrease in concentrations is likely caused by a slight rise in the temperature of the gases inside the package. The maximal concentration of ozone generated during the test at both 50 and 70 kV are approximately the same at around 7000 ppm. Running at 70 kV, the treatment reached the peak ozone concentration in only 9 min compared to 17 min running at 50 kV. This indicates that rate of ozone generation at 70 kV is about two times more than at 50 kV, and also corresponds to its approximately two times greater power consumption. After running for 20 mins, the temperature of gas inside the package reached 31 degrees Celsius at 70 kV, compared to 25 degrees Celsius at 50 kV.

The OAS quantitation is time dependent and provides a measure of RGS generation. Higher $NO_2$ and $NO_3$ concentrations may lead to greater detoxification. Overall, a higher RGS sum indicates greater chemical changes in the product (e.g., detoxification). This would be measured as the total sum area of ionization during the plasma treatment (at the specified voltage and gap). The 70 kV indirect treatment may provide a higher $NO_2$ concentration (area under the curve) than the 50 kV indirect treatment. Post-treatment concentration measurements are time dependent due to the formation of stable ions that cannot be quantified in the OAS. Thus, the OAS provides a signature of the RGS created, but does not provide a full quantitation. Specifically, $N_2O_5$ and —OH overlap in their absorbance signature so that a reduction in ozone concentration at longer times to form these RGS will show up as an overall loss in the total RGS due to the difference in spectral cross-section. Additionally, OHOON (pernitric acid) and —OOON (pernitrous acid) may form, but it is not visible in the OAS spectra window that is being measured.

The ROSA AFQ-FAST test (manufactured by Charm Science, Inc.) was selected to quantitatively detect aflatoxin in the peanut samples. Each peanut sample (200 g) was first ground using a grinder. Then 30 g sample were weighed from the ground sample and was extracted with 150 ml of 84% Acetonitrile-16% water. The extract was centrifuged for 10 s for clarification. The extract was then serially diluted (1:10) with the provided AFQ dilution buffer. Then 300µl diluted extract was pipetted onto the absorbent pad of the test strips and incubated at 40 degrees Celsius for 5 minutes. The test strips were read immediately after incubation using the Charm-M reader. This Rapid One Step Assay is a quantitative lateral flow test that is read in a ROSA-M Reader. The ROSA AFQ-FAST test has been approved by USDA GIPSA (Grain Inspection, Packers and Stockyards Administration) for corn, peanuts and 24 other commodities. This method will only measure pure toxins and will not quantify aflatoxin degradants.

The reduction of aflatoxin measured in the test is presented in the table below:

| | Sample 1 (ppb) | Sample 2 (ppb) | Mean ± Std (ppb) | Reduction (%) |
|---|---|---|---|---|
| Control | 282 | 238 | 260 ± 31 | — |
| 50 kV 1 h | 130 | 80 | 105 ± 35 | 60% |
| 70 kV 1 h | 61 | 73 | 67 ± 8 | 74% |

As shown, aflatoxin was significantly reduced by 60% at 50 kV and 74% at 70 kV through the treatment.

Figure 14C:
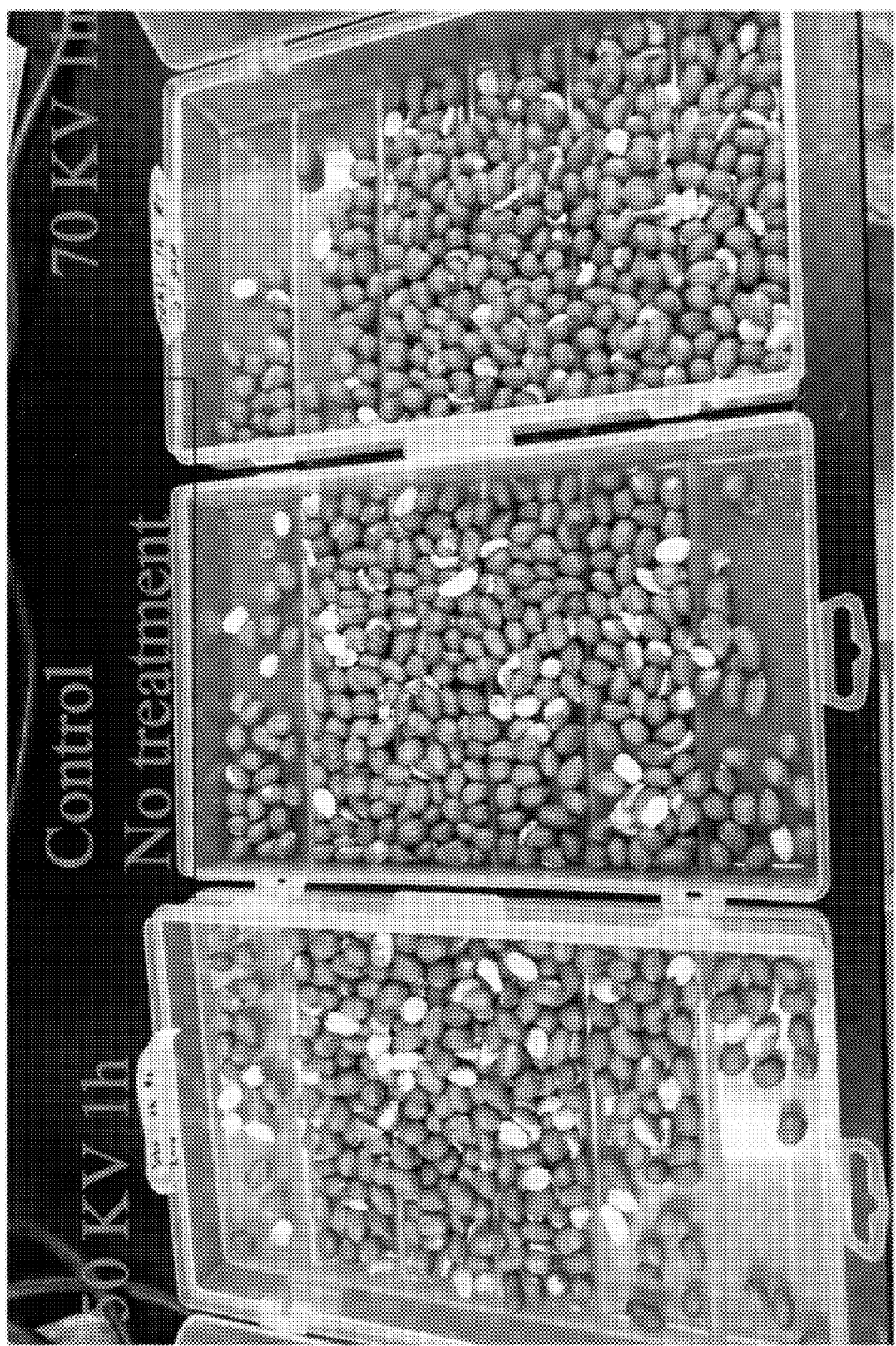
FIG. 14C is a color photograph comparing treated product of the implementations of FIGS. 14A and 14B with a control group.
Figure 15A:
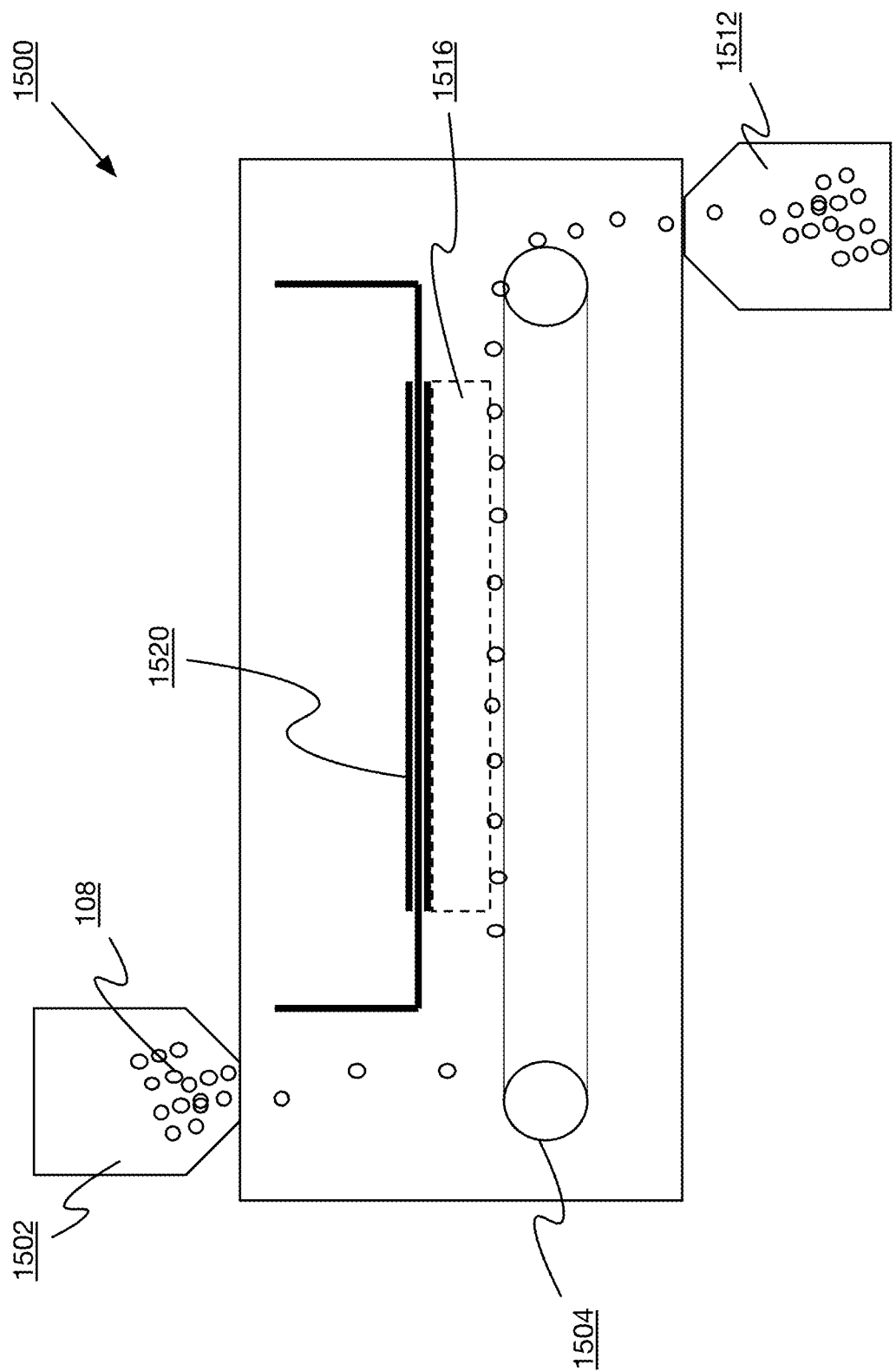
FIG. 15A is an illustration of another system for treating product, according to some implementations.
Figure 15B:
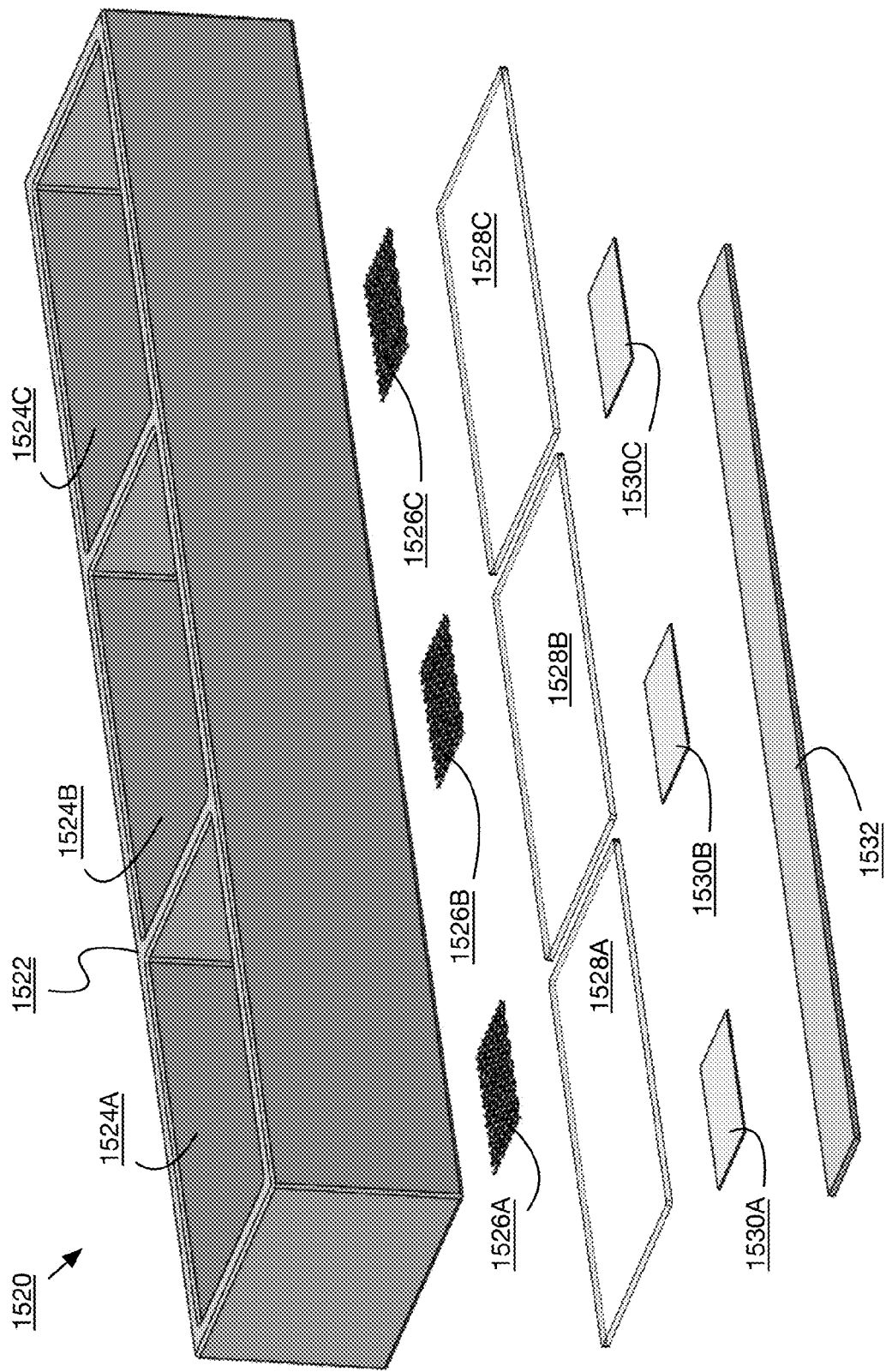
FIGS. 15B-15D are exploded, top, and side views of a cold plasma reactor for use in the system of FIG. 15A, according to some implementations.
Figure 15C:
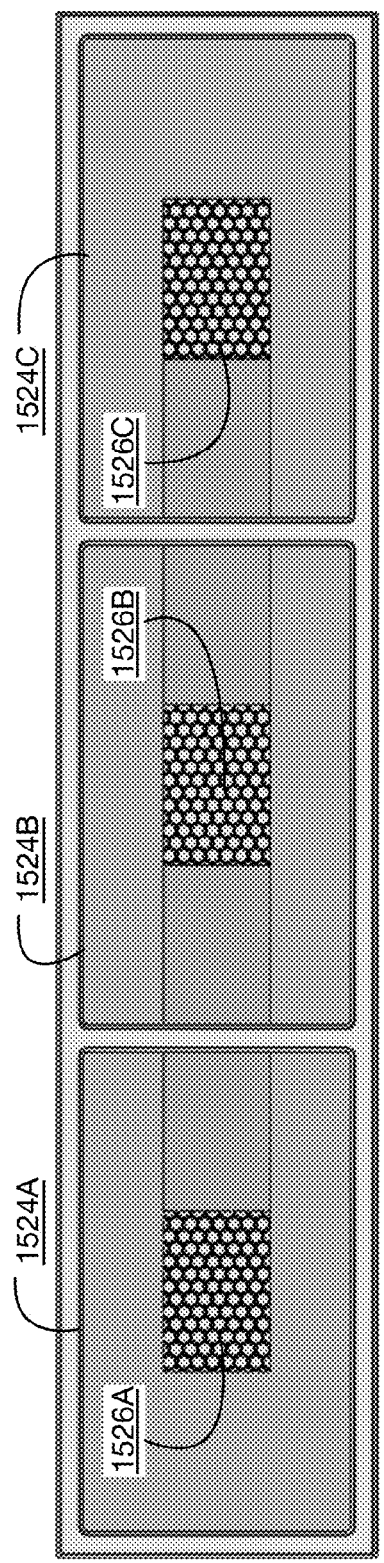
Figure 15D:
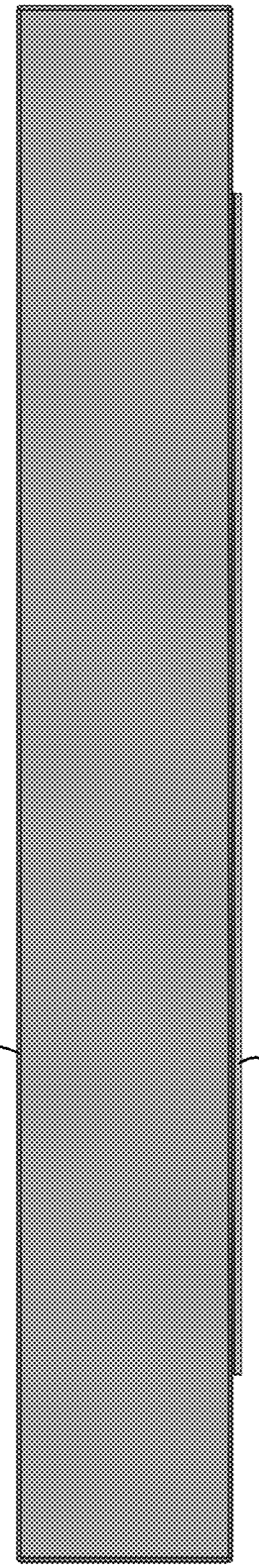
Figure 15E:
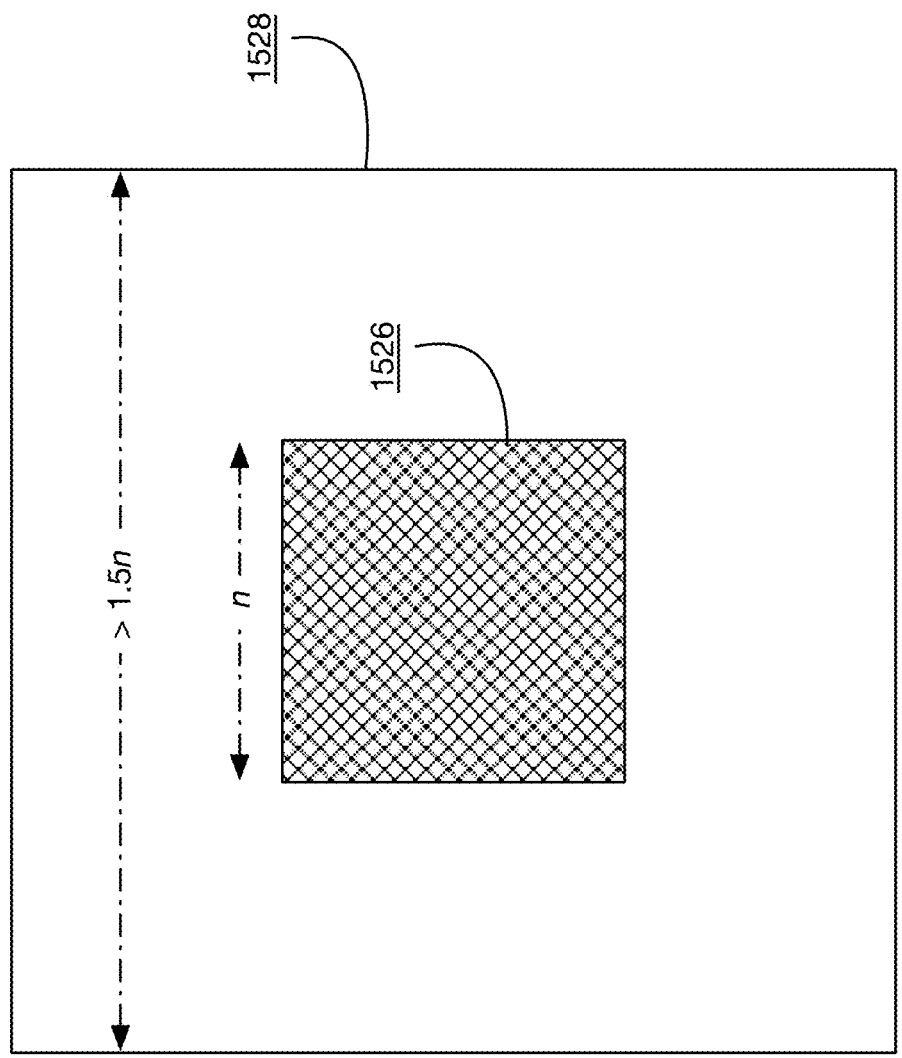
FIG. 15E is a top view of an electrode and dielectric barrier for a cold plasma reactor, according to some implementations.

The treated samples were similar in appearance and quality compared to a control group. FIG. 14C is a color photograph comparing treated product of the implementations of FIGS. 14A and 14B with a control group. After treatment at either 50 or 70 kV, the color of the peanut skin appeared to be brighter, as compared to more reddish and darker skin of the untreated peanut samples. Because of its brighter color, the peanut kernels after treatment were more aesthetically appealing.

To determine the effect of treatment on peanut oil, peroxide and acid levels of each sample were measured, as shown in the table below:

| Sample | Peroxide value (m mol/Kg) | Acid value (mg KOH/g) |
|---|---|---|
| Control | 2.86, 3.52 (3.19 ± 0.47) | 0.54, 0.59 (0.57 ± 0.04) |
| 50 KV 1 h | 3.24, 4.51 (3.88 ± 0.90) | 0.53, 0.58 (0.56 ± 0.04) |
| 70 KV 1 H | 3.68, 4.49 (4.09 ± 0.58) | 0.51, 0.56 (0.54 ± 0.04) |

The peroxide value of the peanut oil was increased slightly after treatment, although this increase is not statistically significant. In addition, the final peroxide value of the treated peanuts was still below 5 mmol/kg, as commonly found in fresh oil. Acid value of peanut oil was not affected by the treatment.

While the above example used small samples, the systems and methods discussed herein have also been tested with larger samples, and the results scale appropriately.

In some further implementations, cold plasma reactors may be deployed with electrodes in close proximity to where the product will be treated. For example, in some implementations and with some gases, a reactor may generate short-lived RGS such as superoxides or hydroxyl radicals that rapidly degrade (e.g. within microseconds). Even with fan-based distribution of the generated gasses, short-lived components may not travel more than a few inches. These short-lived RGS may be particularly desirable for product treatment; accordingly, in some implementations, efficacy may be increased by having the product treatment region in close proximity to where the plasma is generated.

FIG. 15A is an illustration of a system 1500 for treating product with close positioning of product treatment regions, according to some implementations. An input hopper 1502 may allow product to drop into a treatment container (e.g. via an airlock or other gas impermeable or semi-impermeable opening) and be carried by a conveyor 1504 (e.g. belt, screw, etc.) past a reactor 1520 through a region of high concentrations of generated RGS 1516, before being deposited into an output hopper 1512 (having a similar airlock or other gas impermeable or semi-impermeable opening). In the implementation shown, the reactor 1520 may comprise a high voltage single dielectric barrier discharge (SDBD) reactor (comprising a charged electrode, dielectric barrier, and ground electrode in close proximity) that generates plasma on or near the surfaces of its electrodes when a voltage is applied (e.g. 10, 20, 40, 60, 80 kV or any other such value, depending on implementation). In some implementations, RGS may be generated on both sides of the reactor 1520, and RGS from above the reactor may be recirculated to the product treatment region 1216 (e.g. via fans and/or ducting). In some implementations, a plurality of reactors 1520 may be placed in line along the conveyor 1504, allowing for distributed generation of RGS. As discussed above, this may allow for a more consistent RGS concentration throughout the treatment process.

FIGS. 15B-15D are exploded, top, and side views of a cold plasma reactor 1520 for use in the system of FIG. 15A, according to some implementations. Referring first to FIG. 15B, a support or frame 1522 may comprise a plurality of compartments 1524A-1524C, referred to generally as compartments or containers 1524. Each compartment 1524 may support a corresponding dielectric barrier 1528A-1528C, referred to generally as a dielectric barrier 1528, which may comprise pyrex, quartz, polyproplyene, polycarbonate, HDPE, or any other such material capable of withstanding high voltages. Electrodes may be attached in opposition to each other on either side of the dielectric barrier, e.g. top electrodes 1526A-1526C (referred to generally as a first electrode, top electrode, charged electrode, or electrode 1526 or similar terms) and bottom electrodes 1530A-1530C (referred to generally as a second electrode, bottom electrode, ground electrode, or electrode 1530 or similar terms). Although referred to here as charged and ground electrodes 1526, 1530, in some implementations the polarities of these electrodes may be reversed (e.g. ground electrode 1526 and charged electrode 1530). Electrodes 1526, 1530 may be attached to the dielectric barrier 1528 via any suitable means, such as clips, adhesives, adhesive foil tapes, or other conductive or non-conductive fasteners. Dielectric barrier 1528 may be solid in some implementations, or gas permeable (e.g. perforated) in other implementations. Electrodes 1526, 1530 may be attached via supply leads (not illustrated) to a high voltage power supply and, during operation, charged to a high voltage (e.g. 20, 30, 40, 60, 80 kV RMS or any other such value) to generate plasma and RGS within a region above and below the electrodes. In some implementations, a conveyor belt 1532 may be positioned below the reactors to move product through the high concentration RGS region immediately below the reactor. In some implementations, a second reactor or set of reactors (not illustrated) may be positioned closely below the conveyor belt 1532, and the conveyor may be gas permeable (e.g. mesh belts), allowing for increased RGS concentrations. As shown, a series of reactors or sets of electrodes and dielectric barriers may be deployed along the length of the conveyor 1532 to enable longer duration treatments or higher throughput processing.

As shown in FIG. 15C, in some implementations, the electrodes 1526 may be centered on the dielectric barrier (and centered within a container or compartment 1524). In other implementations, the electrodes 1526 may be offset or non-centered.

To enable the use of higher voltages, the dielectric barrier may need to have larger dimensions than the electrodes. For example, FIG. 15E is a top view of an electrode 1526 and dielectric barrier 1528 for a cold plasma reactor, according to some implementations. As shown, the electrode may be square, with length and width dimensions n; and the dielectric barrier may be similarly square, with length and width dimensions of at least 1.5n, and in some implementations, at least 2n. The specific ratio of the barrier dimensions to the electrode dimensions may be dependent on the voltage applied between the electrodes to avoid arcing. Although shown as square electrodes and barriers, other shapes may be used, such as circular electrodes and barriers (e.g. with diameters n and at least 1.5n, respectively); rectangular electrodes and barriers as shown in FIG. 15C (e.g. with length n and width m, and with at least length 1.5n and width 1.5m, respectively); or any other such shapes.

Figure 16A:
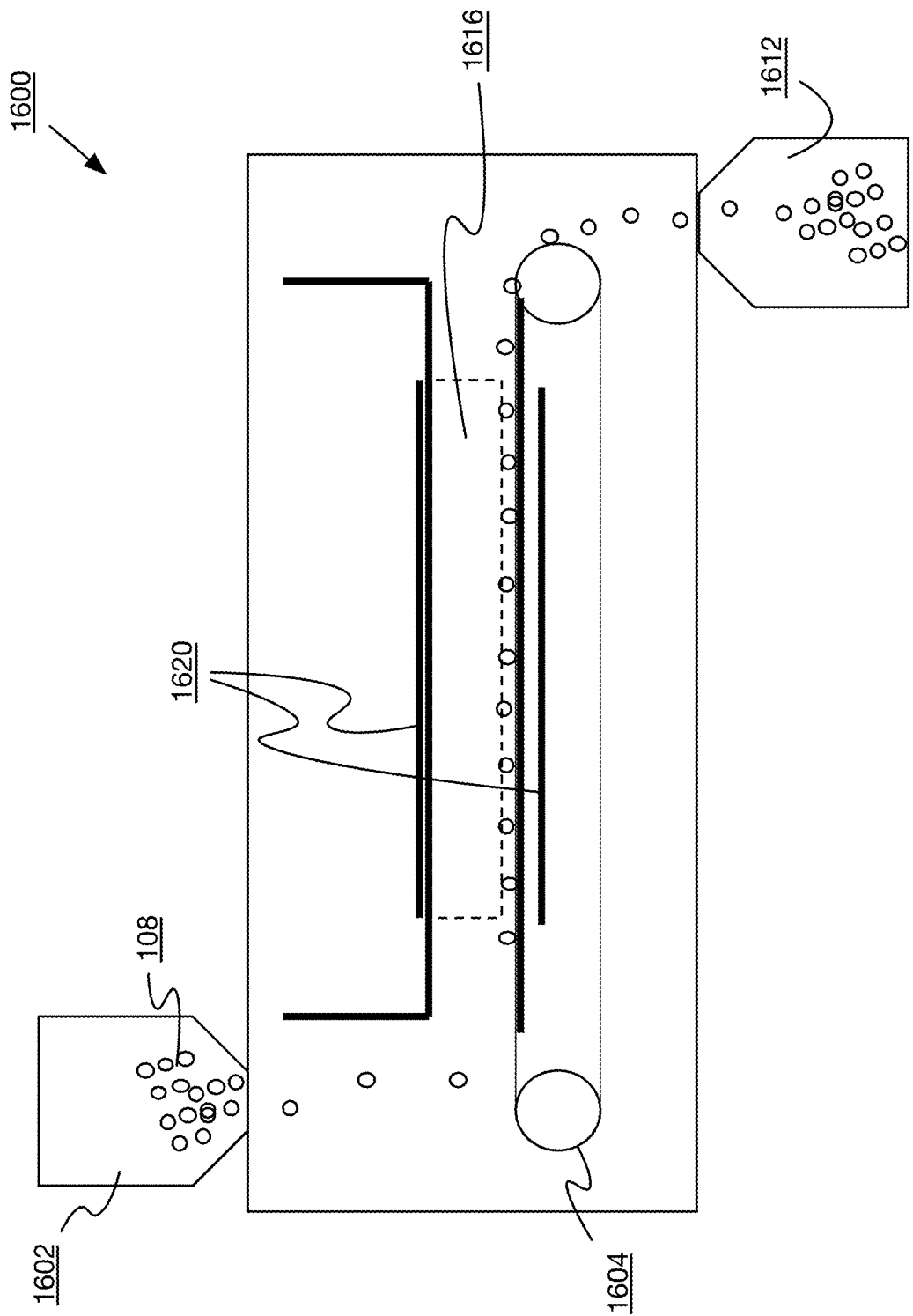
FIG. 16A is an illustration of another system for treating product, according to some implementations.

While the implementations of FIGS. 15A-15D utilize a single dielectric barrier, in other implementations, a double dielectric barrier may be utilized with a product treatment region between the barriers. For example, FIG. 16A is an illustration of another system 1600 for treating product 108, according to some implementations. As with the implementation of FIG. 15A, system 1600 may comprise an input hopper 1602, conveyor 1604, and output hopper 1612, and product 108 may be conveyed through a product treatment region 1616 having a high concentration of RGS. The RGS may be generated by one or more reactors 1620 having two dielectric barriers positioned above and below the conveyor 1604. In many such implementations, conveyor 1604 may be gas permeable (e.g. a mesh conveyor).

Figure 16B:
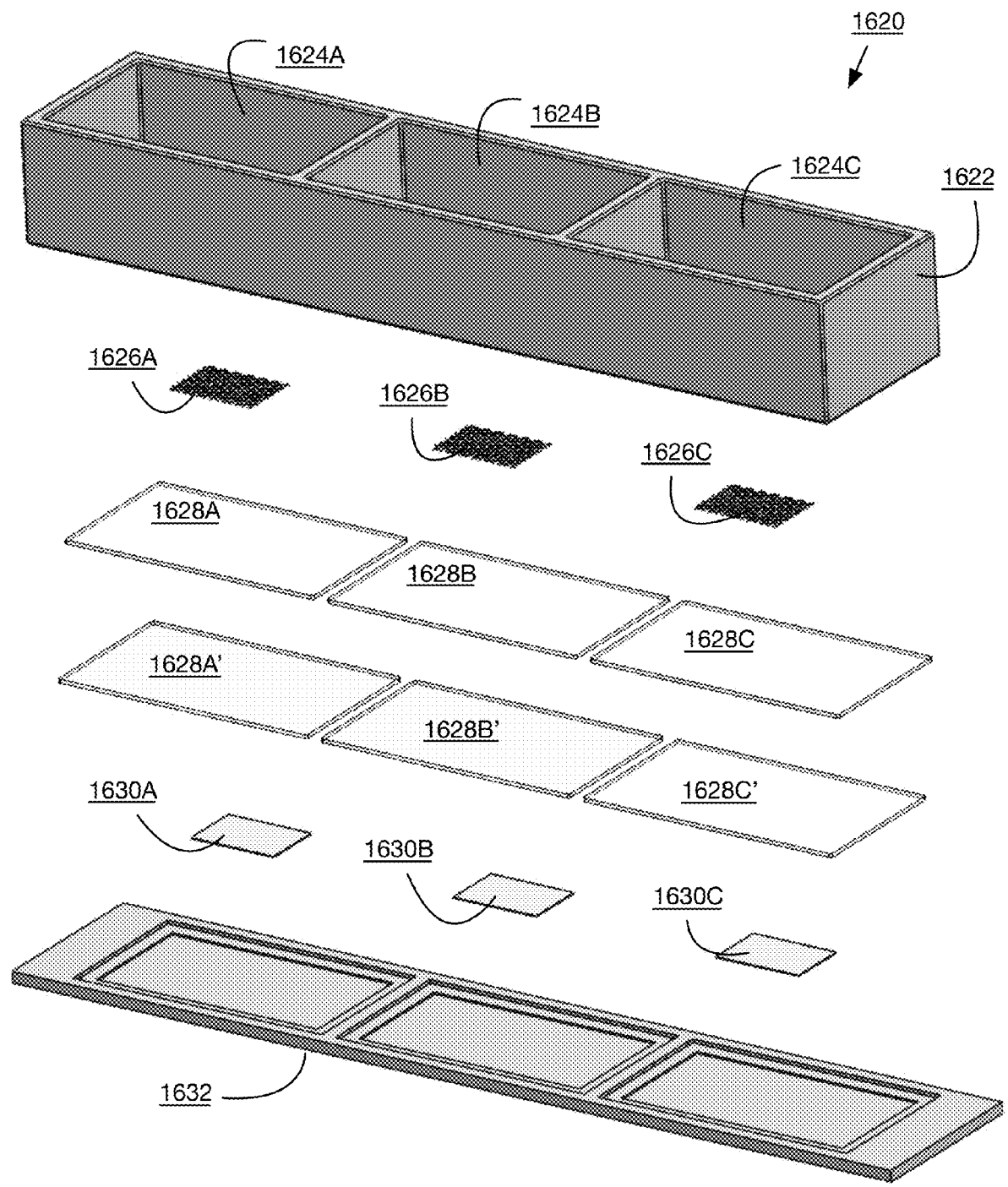
FIGS. 16B-16D are exploded, top, and side views of a cold plasma reactor for use in the system of FIG. 16A, according to some implementations.
Figure 16C:
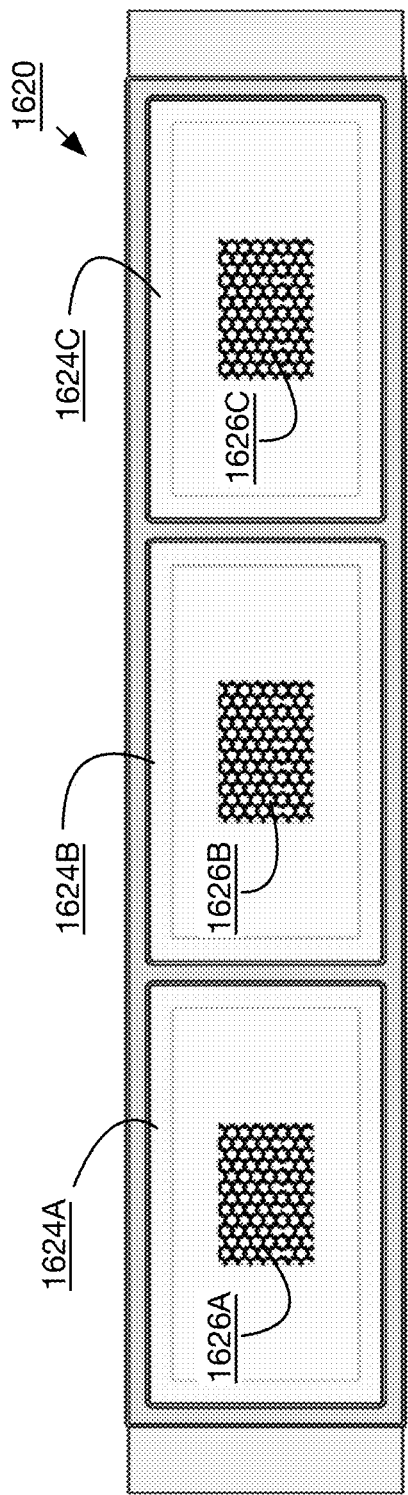
Figure 16D:
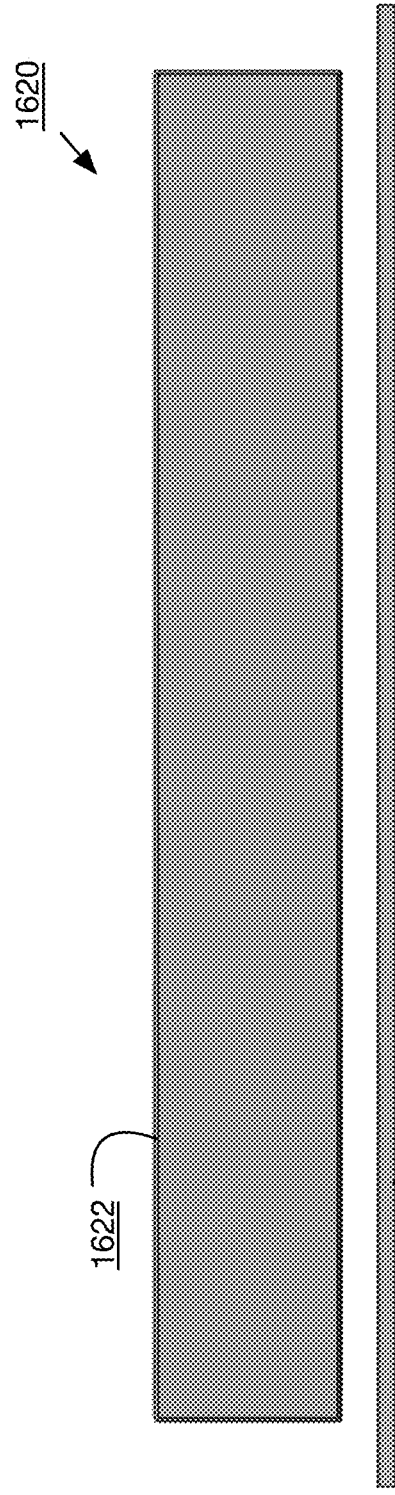

FIGS. 16B-16D are exploded, top, and side views of a cold plasma reactor 1620 for use in the system of FIG. 16A, according to some implementations. Similar to the reactor 1520 of FIG. 15B, reactor 1620 may comprise a frame 1622 (which may be referred to as an upper frame or first frame, in some implementations); a compartment or container 1624; a first electrode 1626; and a second electrode 1630. A first dielectric barrier 1628 may be attached to the upper frame and a first electrode 1626. A second dielectric barrier 1628' may be positioned in opposition across a product treatment region to the first dielectric barrier 1628 (said region including a conveyor for product, not illustrated); and may be attached to the second electrode 1630. A lower frame 1632 may support the second dielectric barrier 1628' and second electrode 1630. When a high voltage is applied between first and second electrode 1626, 1630, RGS may be generated between dielectric barriers 1628, 1628', allowing for treatment of product within the product treatment region. As shown in the side view of FIG. 16D, lower frame 1632 may be positioned in close proximity and parallel to frame 1622. As shown in FIG. 16B and as discussed above in connection with the reactor of FIG. 15B, multiple reactors may be positioned in series, or a reactor may comprise multiple compartments, electrodes, and dielectric barriers positioned in series for continuous treatment or higher throughput with consistent RGS concentrations.

As shown in the implementations of FIGS. 15A-16D, the electrodes and dielectric barriers may comprise thin planes or planar elements positioned parallel to each other and either adjacent or spaced apart in the various implementations shown. Each set of electrodes and dielectric barrier(s) may have similar shapes and dimensions (with the barriers having larger dimensions, as discussed above in connection with FIG. 15E, to prevent arcing), and may be centered with one another (e.g. positioned such that the centers of each planar element are in alignment) in some implementations, or offset in other implementations.

Accordingly, the systems and methods discussed herein are directed to an improved high voltage plasma-based product treatment within a large container capable of processing product at a high throughput rate, without adverse effects on quality from heating of the product. The system is operationally efficient, and is capable of being scaled up or down to provide lower or higher throughput rates, depending on the product manufacturer or processor's needs. In particular, by integrating the plasma reactor into the processing container, the system obviates the need for further containerization or packaging of product during processing.

In one aspect, the present disclosure is directed to a system for product treatment. The system includes a cold plasma reactor, comprising: a first electrode having a dimension n; a second electrode, parallel to the first electrode, having a corresponding dimension n; and a first dielectric barrier positioned between the first electrode and the second electrode having a corresponding dimension of at least 1.5n. The first and second electrodes are configured to support a voltage applied between the electrodes of at least 40 kV RMS.

In some implementations, a center of the first electrode, a center of the second electrode, and a center of the first dielectric barrier are aligned. In some implementations, the dimension n is one of a length, a width, or a diameter.

In some implementations, the system includes a product application region adjacent to the second electrode, the product application region comprising a working gas such that when the voltage is applied between the electrodes, one or more reactive gas species are generated within the product application region. In a further implementation, the second electrode comprises a first surface adjacent to the first dielectric barrier, and an opposing second surface adjacent to the product application region.

In some implementations, the cold plasma reactor further comprises a second dielectric barrier positioned between the first dielectric barrier and the second electrode, the second dielectric barrier having a corresponding dimension of at least 1.5n. In a further implementation, the system includes a product application region between the first dielectric barrier and the second dielectric barrier, the product application region comprising a working gas such that when the voltage is applied between the electrodes, one or more reactive gas species are generated within the product application region.

In some implementations, the cold plasma reactor further includes: a frame positioned between the first dielectric barrier and the second dielectric barrier, the frame including an air gap; and a working gas within the frame and between the first dielectric barrier and the second dielectric barrier; and when the voltage is applied between the electrodes, one or more reactive gas species are generated in the working gas within the frame. In a further implementation, the first dielectric barrier is gas permeable. In a still further implementation, the cold plasma reactor includes a third dielectric barrier adjacent to the first electrode and on an opposing side of the first electrode from the first dielectric barrier, and the third dielectric barrier is gas permeable. In another still further implementation, the second dielectric barrier is not gas permeable.

In some implementations, the system includes a container; and one side of the container comprises the cold plasma reactor. In a further implementation, at least one additional side of the container comprises a second cold plasma reactor. In another further implementation, the first dielectric barrier is gas permeable; and the container comprises a product application region, the product application region comprising a working gas such that when the voltage is applied between the electrodes, one or more reactive gas species are generated within the product application region.

In some implementations, the cold plasma reactor is a first cold plasma reactor, and the system further includes a second cold plasma reactor adjacent to and aligned with the first cold plasma reactor in a vertical direction; and a passage for product between the first cold plasma reactor and the second cold plasma reactor, the passage having an internal dimension larger than the product and smaller than either the first cold plasma reactor or the second cold plasma reactor.

In some implementations, the cold plasma reactor is a first cold plasma reactor, and the system includes a second cold plasma reactor adjacent to and aligned with the first cold plasma reactor in a lateral direction; and a product application region extending the length of the first and second cold plasma reactors in the lateral direction, the product application region comprising a working gas such that when the voltage is applied between the electrodes, one or more reactive gas species are generated within the product application region. In a further implementation, the system includes a product conveyor positioned within and extending along the product application region. In another further implementation, the product application region is at least partially within the first cold plasma reactor and the second cold plasma reactor.

In some implementations, the cold plasma reactor is a first cold plasma reactor, and the system includes one or more additional cold plasma reactors; and a product treatment container surrounding the first cold plasma reactor and the one or more additional cold plasma reactors, the product treatment container comprising a product application region subdivided into a plurality of subregions by the first cold plasma reactor and the one or more additional cold plasma reactors, the plurality of subregions each comprising a working gas such that when the voltage is applied between the electrodes of each adjacent cold plasma reactor, one or more reactive gas species are generated within the subregion.

In another aspect, the present disclosure is directed to a method of treating a product. The method includes providing a product in proximity to a cold plasma reactor; and applying a voltage between the electrodes of at least 40 kV RMS to generate reactive gas species for treating the product.

The present disclosure has been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

The present disclosure may have also been described, at least in part, in terms of one or more embodiments. An embodiment of the present invention is used herein to illustrate the present invention, an aspect thereof, a feature thereof, a concept thereof, and/or an example thereof. A physical embodiment of an apparatus, an article of manufacture, a machine, and/or a process that embodies the present invention may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

It should be noted that certain passages of this disclosure can reference terms such as "first" and "second" in connection with devices for purposes of identifying or differentiating one from another or from others. These terms are not intended to merely relate entities (e.g., a first coil and a second coil) temporally or according to a sequence, although in some cases, these entities can include such a relationship. Nor do these terms limit the number of possible entities (e.g., coils) that can operate within a system or environment.

It should be understood that the systems described above can provide multiple ones of any or each of those components and these components can be provided on either an integrated circuit or, in some embodiments, on multiple circuits, circuit boards or discrete components. In addition, the systems and methods described above can be adjusted for various system parameters and design criteria, such as number of coils, shape of coils, coil layers, etc. Although shown in the drawings with certain components directly coupled to each other, direct coupling is not shown in a limiting fashion and is exemplarily shown. Alternative embodiments include circuits with indirect coupling between the components shown.

It should be noted that although the flowcharts provided herein show a specific order of method steps, it is understood that the order of these steps can differ from what is depicted. Also two or more steps can be performed concurrently or with partial concurrence. Such variation will depend on the software and hardware systems chosen and on designer choice. It is understood that all such variations are within the scope of the disclosure.

While the foregoing written description of the methods and systems enables one of ordinary skill to make and use various embodiments of these methods and systems, those of ordinary skill will understand and appreciate the existence of variations, combinations, and equivalents of the specific embodiment, method, and examples herein. The present methods and systems should therefore not be limited by the above described embodiments, methods, and examples, but by all embodiments and methods within the scope and spirit of the disclosure. It should be understood that the application is not limited to the details or methodology set forth in the description or illustrated in the figures. It should also be understood that the terminology is for the purpose of description only and should not be regarded as limiting.

What is claimed:

1. A product treatment system, comprising:
   a container defining a chamber and being configured to receive a feed gas and a product within the chamber and to discharge the product from the chamber;
   a cold plasma reactor disposed and configured to generate, with the product and the feed gas within the chamber, a plasma within the chamber,
   wherein:
   the plasma diffuses through the chamber and the product and ionizes the feed gas to generate multiple reactive gas species (RGS) that decontaminate the product prior to the product being discharged from the chamber, the cold plasma reactor is provided as first and second cold plasma reactors operably disposed on first and second sides of the container, respectively, each of the first and second cold plasma reactors comprises first and second electrodes separated by an air gap, a dielectric layer interposed between the first and second electrodes and an exterior insulator interposed between the first and second electrodes and the chamber, and wherein the dielectric layer and the exterior insulator are perforated to permit gas communication between the chamber and the air gap.

2. The product treatment system according to claim 1, wherein the multiple RGS comprise ozone and at least one of an oxygen-containing reactive gas species and a nitrogen-containing reactive gas species.

3. The product treatment system according to claim 1, wherein the multiple RGS comprise ozone and a reactive nitrogen-containing gas species, and wherein the system is configured to provide a concentration within the chamber of the reactive nitrogen-containing gas species, which temporarily exceeds a concentration of the ozone within the chamber.

4. The product treatment system according to claim 1, wherein:

the container is provided as one or more containers and the cold plasma reactor is provided as one or more cold plasma reactors for each of the one or more containers, and the one or more containers and the one or more cold plasma reactors for each of the one or more containers are operable in a continuous sequence.

5. The product treatment system according to claim 4, further comprising at least one of:

a loading bin from which each of the one or more containers receives the product; and a bin into which product is dischargeable from each of the one or more containers.

6. The product treatment system according to claim 1, wherein the container defines one or more chambers and the cold plasma reactor is provided as one or more cold plasma reactors for each of the one or more chambers.

7. The product treatment system according to claim 1, wherein:

the product is gravity-fed through the chamber, and the product treatment system further comprises baffles disposed and configured to slow the gravity-feeding of the product through the chamber.

8. The product treatment system according to claim 1, wherein:

the container defines one or more chambers and the cold plasma reactor is provided as one or more cold plasma reactors for each of the one or more chambers, and the product treatment system further comprises a conveyor belt to convey the product through each of the one or more chambers.

9. The product treatment system according to claim 1, wherein the feed gas is at least one of received from an external supply and generated by the cold plasma reactor.

* * * * *